United States Patent
Ramaprabhu et al.

(10) Patent No.: US 9,149,833 B2
(45) Date of Patent: Oct. 6, 2015

(54) METAL NANOPARTICLE DECORATED CARBON NANOTUBES AND METHODS OF PREPARATION AND USE

(71) Applicant: INDIAN INSTITUTE OF TECHNOLOGY MADRAS, Chennai (IN)

(72) Inventors: Sundara Ramaprabhu, Chennai (IN); Mridula Baro, Chennai (IN); Pranati Nayak, Chennai (IN); Tessy Theres Baby, Chennai (IN)

(73) Assignee: Indian Institute of Technology Madras, Tamilnadu, Chennai (IN)

( * ) Notice: Subject to any disclaimer, the term of this patent is extended or adjusted under 35 U.S.C. 154(b) by 7 days.

(21) Appl. No.: 14/077,806

(22) Filed: Nov. 12, 2013

(65) Prior Publication Data

US 2014/0377790 A1    Dec. 25, 2014

(30) Foreign Application Priority Data

Jun. 24, 2013 (IN) ............ 2728/CHE/2013

(51) Int. Cl.
| | | |
|---|---|---|
| G01N 33/543 | (2006.01) |
| G01N 33/52 | (2006.01) |
| G01N 33/00 | (2006.01) |
| B05D 3/06 | (2006.01) |
| B05D 3/00 | (2006.01) |

(52) U.S. Cl.
CPC ............ *B05D 3/06* (2013.01); *G01N 33/54346* (2013.01); *B05D 3/00* (2013.01); *G01N 33/00* (2013.01); *G01N 33/543* (2013.01)

(58) Field of Classification Search
CPC ... G01N 31/22; G01N 31/00; G01N 33/0049; G01N 31/0047; G01N 31/0036; G01N 31/0027; G01N 31/0009; G01N 33/54346; G01N 33/54313; G01N 33/543; G01N 33/53; G01N 33/50; G01N 33/00; B05D 3/06; B05D 3/00
USPC .......... 436/124, 24; 435/20, 19, 18, 4; 252/502, 503, 506, 507
See application file for complete search history.

(56) References Cited

U.S. PATENT DOCUMENTS

| | | | |
|---|---|---|---|
| 7,105,596 B2 * | 9/2006 | Smalley et al. | 524/495 |
| 2003/0044608 A1 | 3/2003 | Yoshizawa et al. | |
| 2013/0130049 A1 * | 5/2013 | Moilanen et al. | 428/532 |

FOREIGN PATENT DOCUMENTS

| | | | | |
|---|---|---|---|---|
| WO | WO 2008/034939 A1 * | 3/2008 | | C08K 7/24 |
| WO | WO2009026423 A2 | 2/2009 | | |

OTHER PUBLICATIONS

Baby, Tessy Theres et al, Snythesis and nanofluid application of silver nanoparticles decorated graphene, Journal of Materials Chemistry, 2011, 21, pp. 9702-9709.*

(Continued)

*Primary Examiner* — Christine T Mui
(74) *Attorney, Agent, or Firm* — Pepper Hamilton LLP

(57) ABSTRACT

Methods of forming metal nanoparticle decorated carbon nanotubes are provided. The methods include mixing a metal precursor with a plurality of carbon nanotubes to form a metal precursor-carbon nanotubes mixture. The methods also include exposing the metal precursor-carbon nanotubes mixture to electromagnetic radiation to deposit metal nanoparticles on a major surface of the carbon nanotubes.

23 Claims, 13 Drawing Sheets

(56) References Cited

OTHER PUBLICATIONS

Baby, Tessy Theres, et al, Experimental study on the field emission properties of metal oxide nanoparticle-decorated graphene, Journal of Applied Physics, 2012, 111, 034311-1 to 034311-5.*

Sasikaladevi S. et al, Facile and simultaneous production of metal/metal oxide dispersed graphene nano composites by solar exfoliation, 2011, 21, 17094-17097.*

Jha N. et al, Development of MWNT Based Disposable Biosensor on Glassy Carbon Electrode for the Detection of Organophosphorus Nerve Agents, 2009, vol. 9, No. 9, pp. 5676-5680.*

Antunes et al., Comparative study of first- and second-order Raman spectra of MWCNT at visible and infrared laser excitation, *Carbon* (Apr. 18, 2006), 44:2202-2211.

Bahr et al., Covalent chemistry of single-wall carbon nanotubes, *J. Mater. Chem.* (May 1, 2002) 12:1952-1958.

Bai et al., Synthesis, field emission and glucose-sensing characteristics of nanostructural ZnO on free-standing carbon nanotubes films, *Applied Surface Science* (Nov. 10, 2009) 256:2643-2648.

Banerjee et al., Covalent Surface Chemistry of Single-Walled Carbon Nanotubes, *Advanced Materials* (2005) 17(1):17-029.

Choi et al., Solution Chemistry of Self-Assembled Graphene Nanohybrids for High-Performance Flexible Biosensors, *ACS Nano* (Apr. 8, 2010) 4(5):2910-2918.

Du et al., One-step electrochemical deposition of a graphene—$ZrO_2$ nanocomposite: Preparation, characterization and application for detection of organophosphorus agents, *J. Mater. Chem.* (2011) 21:8032-8037.

Eswaraiah et al., Top down method for synthesis of highly conducting graphene by exfoliation of graphite oxide using focused solar radiation, *J. Mater. Chem.* (2011) 21:6800-6803.

Guerra et al., Hybrid materials based on Pd nanoparticles on carbon nanostructures for environmentally benign C—C coupling chemistry, *Nanoscale* (2010) 2:1390-1400.

Hummers et al., Preparation of Graphitic Oxide, *J. Am. Chem. Soc.* (Mar. 1958) 80(6):1339.

Khanderi et al., Synthesis and sensoric response of ZnO decorated carbon nanotubes, *J. Mater. Chem.* (Jun. 2, 2009) 19:5039-5046.

Kim et al., Defect-induced loading of Pt nanoparticles on carbon nanotubes, *Applied Physics Letters* (Jan. 11, 2007) 90:023114.

Kim et al., Structural evolution of graphite oxide during heat treatment, *Chemical Physics Letters* (Jun. 12, 2011) 511:110-115.

Kumar et al., Nanostructured Zinc Oxide Particles in Chemically Modified Electrodes for Biosensor Applications, *Analytical Letters* (2008) 41:141-158.

Lee et al., A novel organophosphorus hydrolase-based biosensor using mesoporous carbons and carbon black for the detection of organophosphate nerve agents, *Biosensors and Bioelectronics* (Nov. 14, 2009) 25:1566-1570.

Li et al., Electrochemical acetylene sensor based on Au/MWCNTs, *Sensors and Actuators B: Chemical* (May 13, 2010) 149:427-431.

Liu et al., A glassy carbon electrode modified with graphene and tyrosinase immobilized on platinum nanoparticles for sensing organophosphorus pesticides, *Microchim Acta* (Jul. 21, 2011) 175:129-135.

Liu et al., Sensitive electrochemical detection of enzymatically generated thiocholine at carbon nanotube modified glassy carbon electrode, *Electrochemistry Communications* (Sep. 22, 2005) 7:1163-1169.

Lu et al., Carbon nanotube reinforced NiO fibers for rechargeable lithium batteries, *Solid State Sciences* (Feb. 25, 2009) 11:982-987.

Lu et al., Microwave-assisted synthesis of graphene—ZnO nanocomposite for electrochemical supercapacitors, *J. of Alloys and Compounds* (Mar. 3, 2011) 509:5488-5492.

Lu et al., Nanometal-Decorated Exfoliated Graphite Nanoplatelet Based Glucose Biosensors with High Sensitivity and Fast Response, *ACS Nano* (Sep. 3, 2008) 2(9):1825-1832.

Norouzi et al., A Glucose Biosensor Based on Nanographene and ZnO Nanoparticles Using FFT Continuous Cyclic Voltammetry, *Int. J. Electrochem. Sci.* (Nov. 1, 2011) 6:5189-5199.

Ovalle et al., Electrochemical study on the type of immobilized acetylcholinesterase inhibition by sodium fluoride, *Electrochimica Acta* (Apr. 30, 2008) 53:6344-6350.

Planeix et al., Application of Carbon Nanotubes as Supports in Heterogeneous Catalysis, *J. Am. Chem. Soc.* (1994) 116:7935-7936.

Pradhan et at, High-Performance, Flexible Enzymatic Glucose Biosensor Based on ZnO Nanowires Supported on a Gold-Coated Polyester Substrate, *Applied Materials & Interfaces* (2010) 2(8):2409-2412.

Pumera, Graphene-based nanomaterials and their electrochemistry, *Chem. Soc. Rev.* (2010) 39:4146-4157.

Reddy et al., Alloy hydride catalyst route for the synthesis of single-walled carbon nanotubes, multi-walled carbon nanotubes and magnetic metal-filled multi-walled carbon nanotubes, *Nanotechnology* (2006) 17:5299-5305.

Sinha et al., AChE biosensor based on zinc oxide sol-gel for the detection of pesticides, *Analytica Chimica Acta* (Dec. 22, 2009) 661:195-199.

Stoller et al., Graphene-Based Ultracapacitors, *Nano Letters* (2008) 8(10):3498-3502.

Sun et al., Zinc Oxide Nanostructured Biosensor for Glucose Detection, *J. Mater. Sci. Technol.* (2008) 24(4):649-655.

Tasis et al., Chemistry of Carbon Nanotubes, *Chem. Rev.* (2006) 106:1105-1136.

Vinayan et al., Synthesis of graphene-multiwalled carbon nanotubes hybrid nanostructure by strengthened electrostatic interaction and its lithium ion battery application, *J. Mater. Chem.* (2012) 22:9949-9956.

Wang et al., Carbon nanotube-supported Pt—Co bimetallic catalysts for preferential oxidation of CO in a $H_2$-rich stream with $CO_2$ and $H_2O$ vapor, *Journal of Power Sources* (Nov. 25, 2011) 202:200-208.

Wang et al., Self assembly of acetylcholinesterase on a gold nanoparticles-graphene nanosheet hybrid for organophosphate pesticide detection using polyelectrolyte as a linker, *J. Mater. Chem.* (2011) 21:5319-5325.

Wang et al., $TiO_2$—decorated graphene nanohybrids for fabricating an amperometric acetylcholinesterase biosensor, *Analyst* (2011) 136:3349-3354.

Wang et al., Zinc oxide nanocomb biosensor for glucose detection, *Applied Physics Letters* (Jun. 6, 2006) 88:233106.

Yin et al., Amperometric biosensor based on immobilized acetylcholinesterase on gold nanoparticles and silk fibroin modified platinum electrode for detection of methyl paraoxon carbofuran and phoxim, *Journal of Electroanalytical Chemistry* (Oct. 2, 2009) 637:21-27.

Yu et al., Self-Assembled Graphene/Carbon Nanotrube Hybrid Films for Supercapacitors, *J. Phys. Chem. Lett.* (Dec. 22, 2009) 1:467-470.

Zhang et al., A facile one-pot route for the controllable growth of small sized and well-dispersed ZnO particles on GO—derived graphene, *J. Mater. Chem.* (2012) 22:11778-11784.

Zhu et al., Multiwalled Carbon Nanotubes Beaded with ZnO Nanoparticles for Ultrafast Nonlinear Optical Switching, *Adv. Mater.* (2006) 18:587-592.

International Search Report for International Application No. PCT/IB2014/061152, mailed on Oct. 28, 2014.

Albiss, $NO_2$ Gas Sensing Properties of ZnO/Single-Wall Carbon Nanotube Composites, *Sensors Journal, IEEE* (Dec. 2010), 10(12):1807-1812.

Jia et al., Preparation and application of a highly sensitive nonenzymatic ethanol sensor based on nickel nanoparticles/Nafion/graphene composite film, *Sensors and Actuators B: Chemical* (Dec. 17, 2012), 177:1035-1042.

Pei et al., Study of a QCM dimethyl methylphosphonate sensor based on a ZnO-modified nanowire-structured manganese dioxide film, *Sensors (Basel)* (Sep. 2, 2010), 10(9):8275-8290.

Wang et al., Three dimensional few layer graphene and carbon nanotube foam architectures for high fidelity supercapacitors, *Nano Energy* (Oct. 17, 2012), 2(2):294-303.

* cited by examiner

METAL NANOPARTICLE DECORATED CARBON NANOTUBES AND METHODS OF PREPARATION AND USE

CROSS-REFERENCE TO RELATED APPLICATIONS

The present application claims the benefit of and priority under title 35 U.S.C. §119(a) to Indian Application No. 2728/CHE/2013, filed on Jun. 24, 2013, entitled "Metal Nanoparticle Decorated Carbon Nanotubes and Methods of Preparation and Use". The aforementioned application is incorporated by reference herein in its entirety.

BACKGROUND

In recent years, there has been increased interest in integration of metal nanoparticles with carbon nanotubes (CNTs) owing to the structural, electrochemical and catalytic properties of the CNTs. The ability of carbon nanotubes to support inorganic nanoparticles such as metal, metal oxides and metal alloy nanoparticles offers opportunities to synthesize hybrid materials that may be used in applications such as for energy conversion (such as, in fuel cells and photo voltaic cells), storage (such as, supercapacitor and lithium ion battery), field emission displays, and gas and vapor sensors.

Some conventional techniques for synthesis of CNTs decorated with metal nanoparticles include surface functionalization of purified CNTs by vigorous acid treatment and chemical reduction and/or oxidation of metal salts using strong reducing/oxidizing agents or by electrodeposition of metal nanoparticles on CNTs. Such techniques may require use of harsh and toxic chemicals thereby limiting the use of the hybrid materials for certain applications. Moreover, some of the techniques require multiple processing steps for forming the hybrid materials and may need intensive energy, thus making them challenging for large scale preparation. In some of these techniques, there are additional costs associated with use and removal of the solvents and the reducing reagents.

Metal salts are commonly used as precursors for depositing metal nanoparticles on chemically inert graphitic surface of the CNTs. However, current synthesis techniques may cause destruction of the CNT structures and therefore change their intrinsic electronic and mechanical properties. Further, inorganic coatings on acid-treated CNTs are often non-uniform.

Some hybrid structures formed by integration of CNTs and metal nanoparticles are used for environmental, defense, biological and medical applications. Such hybrid structures can be used as sensors for detecting organophosphorus compounds. One such organophosphorus compound is paraoxon that may be used as chemical warfare agent due to its high toxicity towards mammals causing neurological disorders. Some of the current detection techniques include gas chromatography, high performance liquid chromatography, and spectroscopy. Many of these techniques are tedious, time consuming and are substantially expensive.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

Briefly, in accordance with one aspect, a method of forming metal nanoparticle decorated carbon nanotubes is provided. The method includes mixing a metal precursor with a plurality of carbon nanotubes to form a metal precursor-carbon nanotubes mixture. The method also includes exposing the metal precursor-carbon nanotubes mixture to electromagnetic radiation to deposit metal nanoparticles on a major surface of the carbon nanotubes.

In accordance with another aspect, a system for forming metal nanoparticle decorated carbon nanotubes is provided. The system includes a container configured to contain a mixture of a metal precursor and a plurality of carbon nanotubes. The system also includes a source configured to apply electromagnetic radiation to the mixture, to facilitate reduction of the metal precursor to metal nanoparticles and to deposit the metal nanoparticles on a major surface of the plurality of carbon nanotubes.

In accordance with another aspect, a method of forming a metal nanoparticle decorated carbon nanotubes is provided. The method includes mixing a zinc precursor with graphite oxide and a plurality of carbon nanotubes to form a mixture. The method also includes exposing the mixture to solar radiation to reduce graphite oxide to solar graphene and to form a carbon nanotubes-graphene composite and to concurrently reduce the zinc precursor to zinc oxide nanoparticles to deposit the zinc oxide nanoparticles on a major surface of the carbon nanotubes-graphene composite.

In accordance with another aspect, a sensor is provided. The sensor includes a carbon nanotubes-graphene composite material and a plurality of zinc oxide (ZnO) nanoparticles deposited on a major surface of the carbon nanotubes-graphene composite material.

In accordance with another aspect a method for detecting an organophosphorus compound in a medium is provided. The method includes contacting a sensor with the medium. The sensor includes a carbon nanotubes-graphene composite material with a plurality of zinc oxide nanoparticles dispersed on a major surface of the composite material. The method also includes sensing an inhibition current by the sensor to detect the presence and a concentration of the organophosphorus compound in the medium.

DETAILED DESCRIPTION

Figure 1:
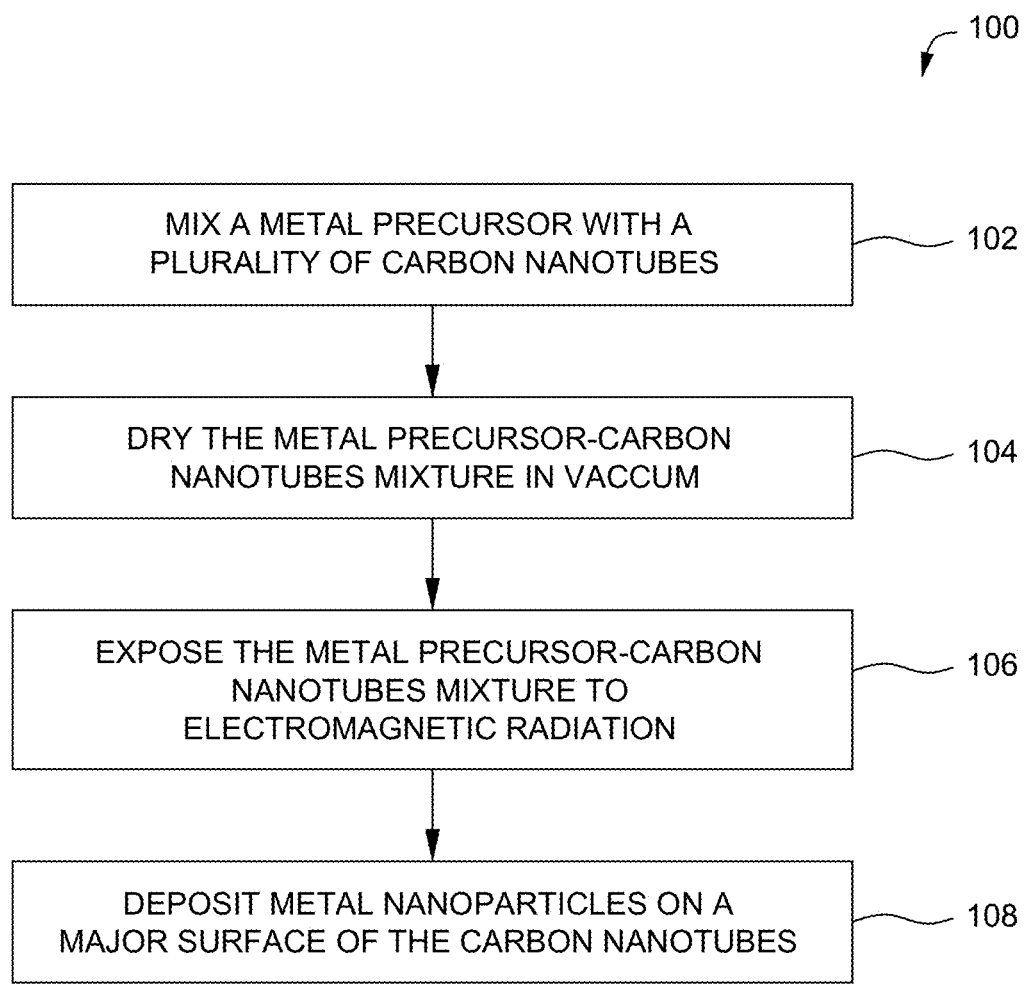
FIG. 1 is an example flow diagram of an embodiment of a method of forming metal nanoparticle decorated carbon nanotubes.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

It will also be understood that any compound, material or substance which is expressly or implicitly disclosed in the specification and/or recited in a claim as belonging to a group or structurally, compositionally and/or functionally related compounds, materials or substances, includes individual representatives of the group and all combinations thereof. While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

Some embodiments are generally directed to techniques of forming metal nanoparticle decorated carbon nanotubes. The present techniques provide hybrid materials formed of carbon nanotubes decorated with a variety of metals, metal oxides and metal alloy nanoparticles using electromagnetic radiation. The technique provides a simple and cost effective synthesis process for decorating metal nanoparticles on carbon nanotubes without use of harsh chemicals and solvents. Such hybrid materials may be used in a variety of industrial and biological applications. Certain hybrid materials formed using the present technique may be used for detection and sensing applications such as for detection of organophosphorus compounds.

Referring now to FIG. 1, an example flow diagram 100 of an embodiment of a method of forming metal nanoparticle decorated carbon nanotubes is illustrated. At block 102, a metal precursor is mixed with a plurality of carbon nanotubes to form a metal precursor-carbon nanotubes mixture. Examples of the metal precursor include, but are not limited to, silver acetate ($CH_3COOAg$), silver chloride (AgCl), silver nitrate ($AgNO_3$), chloroauric acid ($HAuCl_4$), hexachloroplatinic acid ($H_2PtCl_6(H_2O)_6$), palladium chloride ($PdCl_2$), nickel acetate tetrahydrate ($Ni(CH_3COO)_2.4H_2O$), nickel chloride ($NiCl_2$), zinc acetate dihydrate ($Zn(O_2CCH_3)_2.2H_2O$), zinc nitrate ($ZnNO_3)_2$, cobalt nitrate hexahydrate ($Co(NO_3)_2.6H_2O$), cobalt chloride ($CoCl_2$), or combinations thereof.

The carbon nanotubes can include single-walled carbon nanotubes, multi-walled carbon nanotubes, or both. In certain embodiments, the plurality of carbon nanotubes are synthesized by catalytic chemical vapor deposition and are subsequently purified by air oxidation and acid treatment to remove amorphous carbon and catalytic impurities from the carbon nanotubes. The metal precursor-carbon nanotubes mixture is subsequently dried under vacuum (block 104). At block 106, the metal precursor-carbon nanotubes mixture is exposed to electromagnetic radiation to reduce and/or oxidize the metal precursor to deposit metal nanoparticles on a first major surface of the carbon nanotubes (block 108).

In one example, the metal nanoparticles include platinum (Pt), palladium (Pd), silver (Ag), gold (Au), nickel (Ni), titanium (Ti), tin (Sn), ruthenium (Ru), zinc (Zn), copper (Cu), or combinations thereof. In another example, the metal nanoparticles include zinc oxide (ZnO), nickel oxide (NiO), copper oxide (CuO), iron oxide ($Fe_3O_4$), cobalt oxide ($CoO_3$), titanium oxide ($TiO_2$), cerium oxide ($CeO_2$), manganese dioxide ($MnO_2$), or combinations thereof. In yet another example, the metal nanoparticles comprise platinum cobalt alloy ($Pt_3Co$), platinum nickel alloy ($Pt_3Ni$), palladium cobalt alloy ($Pd_3Co$), palladium iron alloy ($Pd_3Fe$), platinum iron alloy ($Pt_3Fe$), or combinations thereof.

In one example embodiment, the electromagnetic radiation is solar radiation. In certain embodiments, the exposure of the metal precursor-carbon nanotubes mixture to electromagnetic radiation such as solar radiation heats the mixture to a temperature of about 150° C. to about 450° C. Specific examples of the temperature for the mixture include about 150° C., about 200° C., about 250° C., about 300° C., about 350° C., about 400° C., about 450° C., and ranges between any two of these values (including endpoints). In one example, the electromagnetic radiation is applied to the metal precursor-carbon nanotubes mixture for a time period of about 1 minute to about 2 minutes to reduce the metal precursor to metal nanoparticles. Specific examples of the exposure time include about 1 minute, about 1.25 minutes, 1.5 minutes, about 1.75 minutes, about 2 minutes, and ranges between any two of these values (including endpoints). The rapid heating effect of the electromagnetic radiation such as solar radiation facilitates reduction of the metal precursor to the metal nanoparticles.

In some examples, atmospheric oxygen along with any oxygen present in the metal precursor-carbon nanotubes mixture facilitates formation of metal oxide nanoparticles on the carbon nanotubes. Examples of the metal oxide nanoparticles include zinc oxide (ZnO), nickel oxide (NiO), copper oxide (CuO), iron oxide ($Fe_3O_4$), cobalt oxide ($CoO_3$), titanium oxide ($TiO_2$), cerium oxide ($CeO_2$), manganese dioxide ($MnO_2$), or combinations thereof. Moreover, combination of two or more metal precursors in a pre-determined stoichiometric ratio is used to deposit metal alloy nanoparticles on the surface of the carbon nanotubes. Examples of the metal alloy nanoparticles include platinum cobalt alloy ($Pt_3Co$), platinum nickel alloy ($Pt_3Ni$), palladium cobalt alloy ($Pd_3Co$), palladium iron alloy ($Pd_3Fe$), platinum iron alloy ($Pt_3Fe$), or combinations thereof.

In certain embodiments, the metal nanoparticles deposited on the carbon nanotubes are of an average diameter of about 2 nanometers (nm) to about 50 nm for the metal nanoparticle decorated carbon nanotubes. Specific examples of size of the metal nanoparticles include, about 2 nm, about 5 nm, about 10 nm, about 20 nm, about 30 nm, about 40 nm, about 50 nm, and ranges between any two of these values (including endpoints).

Figure 2:
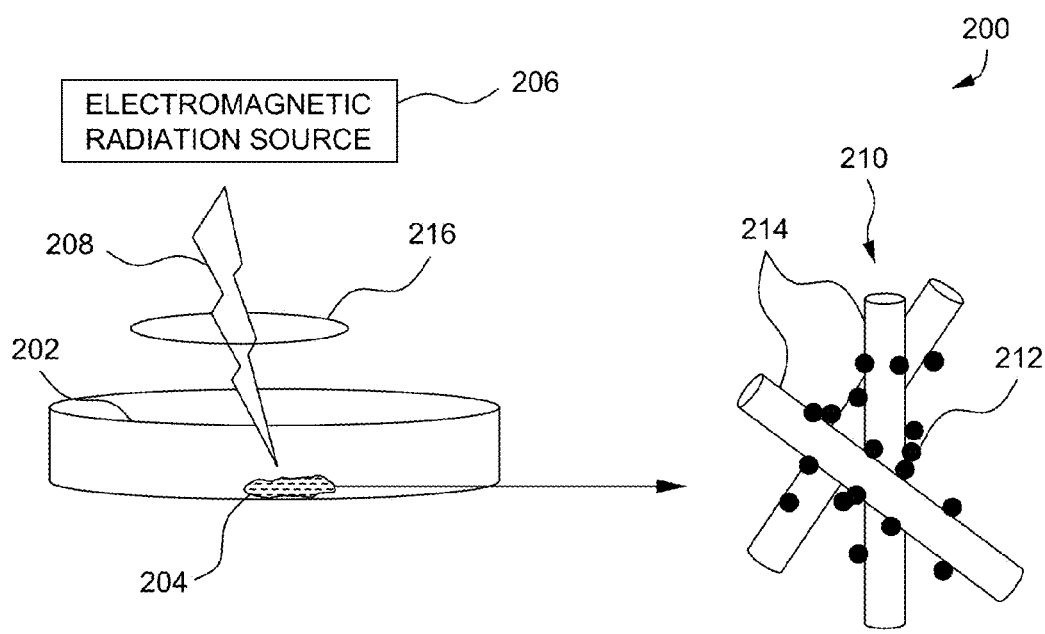
FIG. 2 is an example system for forming metal nanoparticle decorated carbon nanotubes.

Referring now to FIG. 2, an example system 200 for forming metal nanoparticle decorated carbon nanotubes is provided. The system 200 includes a container 202 configured to contain a mixture 204 of a metal precursor and a plurality of carbon nanotubes. Examples of the metal precursor include, but are not limited to, silver acetate ($CH_3COOAg$), silver chloride (AgCl), silver nitrate ($AgNO_3$), chloroauric acid ($HAuCl_4$), hexachloroplatinic acid ($H_2PtCl_6.(H_2O)_6$), palladium chloride ($PdCl_2$), nickel acetate tetrahydrate ($Ni(CH_3COO)_2.4H_2O$), nickel chloride ($NiCl_2$), zinc acetate dihydrate ($Zn(O_2CCH_3)_2.2H_2O$), zinc nitrate ($ZnNO_3)_2$, cobalt nitrate hexahydrate ($Co(NO_3)_2.6H_2O$), cobalt chloride ($CoCl_2$), or combinations thereof. The carbon nanotubes include single-walled carbon nanotubes or multi-walled carbon nanotubes.

The system 200 further includes an electromagnetic radiation source 206 configured to apply electromagnetic radiation 208 to the mixture 204. The exposure of the mixture 204 to the electromagnetic radiation 208 facilitates reduction of the metal precursor to form metal nanoparticle decorated carbon nanotubes 210. In the illustrated embodiment, the metal nanoparticle decorated carbon nanotubes 210 includes metal nanoparticles 212 deposited on a major surface of each of the plurality of carbon nanotubes 214.

In certain examples, the metal nanoparticles 212 include metal oxide nanoparticles, metal alloy nanoparticles, or combinations thereof. Examples of the metal nanoparticles 212 comprise platinum (Pt), palladium (Pd), silver (Ag), gold (Au), nickel (Ni), titanium (Ti), tin (Sn), ruthenium (Ru), zinc (Zn), copper (Cu), zinc oxide (ZnO), nickel oxide (NiO), copper oxide (CuO), iron oxide ($Fe_3O_4$), cobalt oxide ($CoO_3$), titanium oxide ($TiO_2$), cerium oxide ($CeO_2$), manganese dioxide ($MnO_2$), platinum cobalt alloy ($Pt_3Co$), platinum nickel alloy ($Pt_3Ni$), palladium cobalt alloy ($Pd_3Co$), palladium iron alloy ($Pd_3Fe$), platinum iron alloy ($Pt_3Fe$), or combinations thereof.

In one example embodiment, the electromagnetic radiation source 206 is configured to apply solar radiation to the mixture 204. The system 200 optionally includes one or more focusing lens 216 configured to focus the solar radiation 208 towards the container 202. In one example embodiment, a focal length of the one or more focusing lens 216 is about 17 centimeters for a lens diameter of about 90 millimeters. In some examples, a solar power of the solar radiation 208 applied to the mixture 204 is about 1 Watt (W) to about 2 W. Specific examples of solar power include, about 1 W, about 1.25 W, about 1.5 W, about 1.75 W, about 2 W, and ranges between any two of these values (including endpoints).

In one example embodiment, zinc oxide metal nanoparticles are deposited on a carbon nanotubes-graphene composite using the system 200. In this example, a zinc precursor is mixed with graphite oxide and a plurality of carbon nanotubes to form the mixture 204. Examples of the zinc precursor include, but are not limited to, zinc acetate ($Zn(O_2CCH_3)_2$), zinc chloride ($ZnCl_2$) or combinations thereof. The mixture is subsequently exposed to focused solar radiation 208 for a time period of about 1 minute to 2 minutes. Specific examples of the exposure time include about 1 minute, about 1.25 minutes, 1.5 minutes, about 1.75 minutes, about 2 minutes, and ranges between any two of these values (including endpoints).

In this embodiment, the solar power of the focused solar radiation 208 is about 1.77 watts to about 2.03 watts. The mixture 204 is heated to a temperature of about 150° C. to about 450° C. upon exposure to the solar radiation. Specific examples of the temperature for the mixture include about 150° C., about 200° C., about 250° C., about 300° C., about 350° C., about 400° C., about 450° C., and ranges between any two of these values (including endpoints).

In this example, the exposure to solar radiation reduces graphite oxide to solar graphene to form a carbon nanotubes-graphene composite. Moreover, the zinc precursor is concurrently reduced to zinc oxide nanoparticles and the zinc oxide nanoparticles are deposited on a major surface of the carbon nanotubes-graphene composite. The hybrid material formed of zinc oxide decorated carbon nanotubes-graphene composite may be incorporated in a sensor for sensing organophosphorus materials as will be described below.

Figure 3:
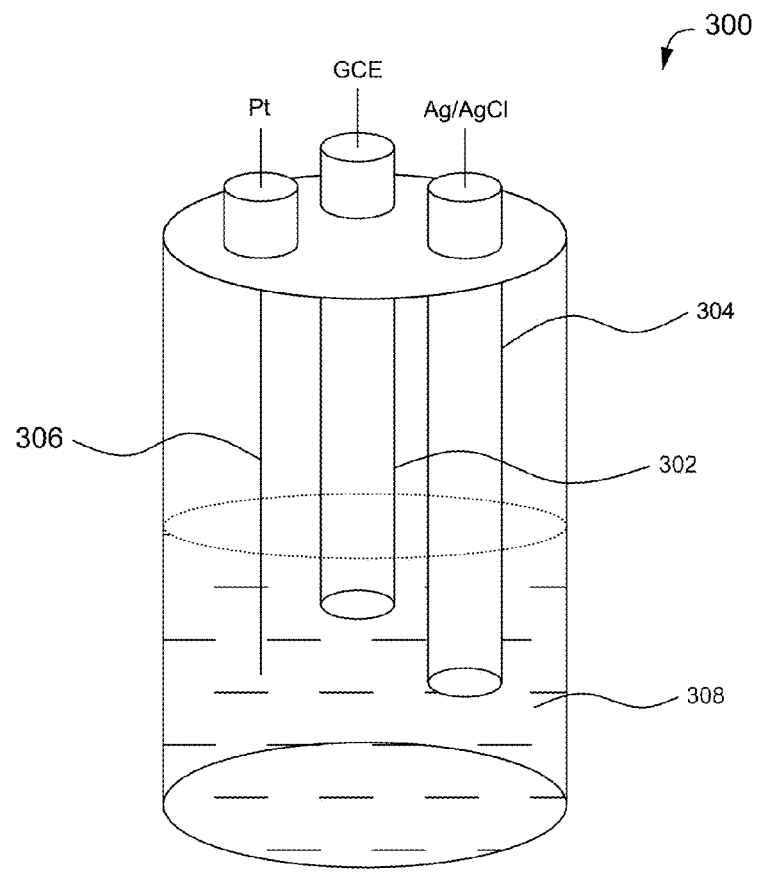
FIG. 3 is an example configuration of a sensor.

FIG. 3 illustrates an example configuration 300 of a sensor. As illustrated, the sensor 300 includes a glassy carbon electrode (GCE) 302, a silver/silver chloride (Ag/AgCl) reference electrode 304 and a platinum (Pt) wire 306 as a counter electrode. In the illustrated embodiment, carbon nanotubes-graphene composite material with a plurality of zinc oxide (ZnO) nanoparticles deposited on the carbon nanotubes-graphene composite material is used as the electrode 302. As described above, such material may be formed by exposing a mixture of a zinc precursor, graphite oxide and a plurality of carbon nanotubes to electromagnetic radiation. In some embodiments, the electrochemical response of the sensor may be observed using a phosphate buffer solution 308 containing about 5 mM potassium ferrocyanide ($K_4[Fe(CN)_6]$).

In one example embodiment, the average diameter of the zinc oxide nanoparticles is about 10 nm to about 60 nm. Specific examples of diameter of zinc oxide nanoparticles include, about 10 nm, about 20 nm, about 30 nm, about 40 nm, about 50 nm, about 60 nm, and ranges between any two of these values (including endpoints). In some embodiments, the sensor 300 is fabricated using about 20 microliters (μL) solution of the carbon nanotubes-graphene composite material decorated with a plurality of zinc oxide (ZnO) nanoparticles and provides an electrochemical active surface area of about 30 $mm^2$.

The sensor 300 can be configured to detect presence of an organophosphorus compound in a medium. Examples of the organophosphorus compound include, but are not limited to, paraoxon, parathion, carbaryl, malathion or combinations thereof. In certain embodiments, the sensor 300 is configured to detect a concentration of about 1 nanomolar (nM) to about 1 picomolar (pM) of the organophosphorus compound in the medium. In operation, the sensor 300 is contacted with the medium and an inhibition current is sensed by the sensor to detect the presence and a concentration of the organophosphorus compound in the medium. In one example embodiment, the inhibition current sensed by the sensor to detect paraoxon in a medium is about 33% to about 82% of an initial value of the inhibition current. This reduction in the sensed inhibition current may be due to electrostatic adhesion of enzyme over hybrid nanostructure and the electrocatalytic activity of the medium towards thiocholine oxidation.

EXAMPLES

Example 1

Formation of Metal Nanoparticle Decorated Carbon Nanotubes

Metal nanoparticle decorated carbon nanotubes were formed using the example method of FIG. 1. A fine mixture of metal salt and multiwall carbon nanotubes (MWCNTs) was formed using a mortar and pestle. This mixture was sprinkled smoothly on a glass petri dish. The mixture was exposed to focused solar radiation using a convex lens of 90 mm diameter for about 5 minutes. The temperature of the mixture had increased in about 2 seconds to about 300° C. This rapid heating facilitated the reduction of metal salts to metal nanoparticles and their deposition on the carbon nanotubes.

During the reaction, fumes emerging from the mixture were observed, indicating the reduction of the metal salt to metal nanoparticles. The heating by the focused radiation created surface defects in the carbon nanotubes and such defects formed anchoring sites for deposition of the metal nanoparticles. It should be noted that without using any additional reducing reagent, the photo thermal decomposition of the metal salts resulted in deposition of metal nanoparticles on the carbon nanotubes. A variety of metal nanoparticles such as silver (Ag), gold (Au), palladium (Pd), platinum (Pt), nickel oxide (NiO), and zinc oxide (ZnO) nanoparticles were deposited on the carbon nanotubes in separate experiments.

Example 2

Characterization of Metal Nanoparticle Decorated Carbon Nanotubes

Figure 4:
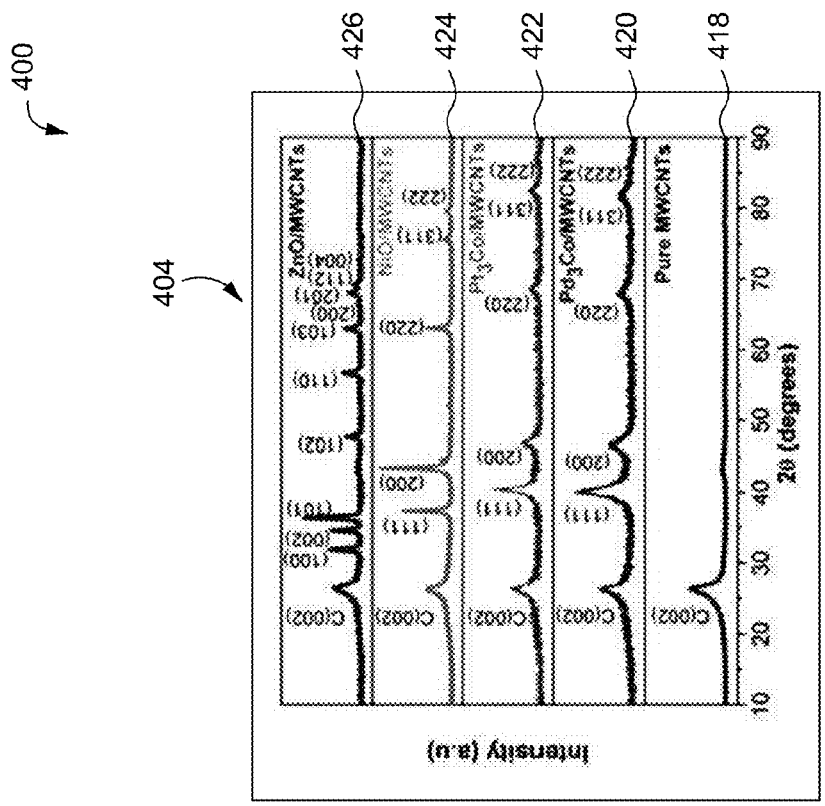
FIG. 4 illustrates example X-ray diffraction (XRD) patterns of metal nanoparticle decorated carbon nanotubes.
Figure 4:
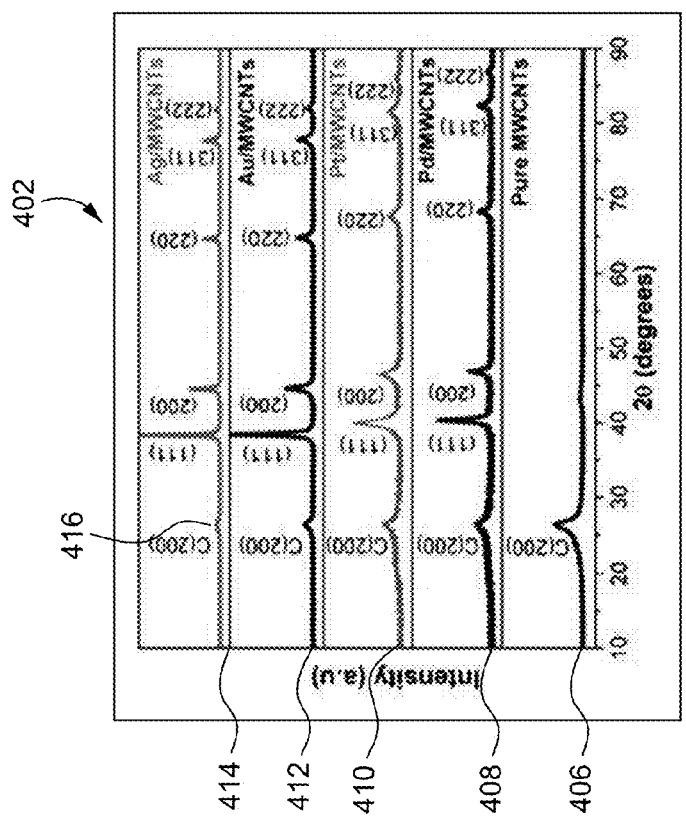

FIG. 4 illustrates example X-ray diffraction (XRD) patterns 400 of metal nanoparticle decorated carbon nanotubes produced in Example 1. The XRD pattern for carbon nanotubes along with XRD patterns for metal decorated carbon nanotubes are represented by reference numeral 402. The XRD pattern for carbon nanotubes along with XRD patterns for metal alloy decorated carbon nanotubes are represented by reference numeral 404. The XRD patterns 400 were recorded using a PANalytical X'Pert Pro X-ray diffractometer with nickel-filtered Cu K$\alpha$ radiation as the X-ray source in the 2$\theta$ range of 5° to 90° with 0.016° step size.

The XRD patterns 400 of plain carbon nanotubes, carbon nanotubes decorated with palladium nanoparticles, carbon nanotubes decorated with platinum nanoparticles, carbon nanotubes decorated with gold nanoparticles and carbon nanotubes decorated with silver nanoparticles are represented by reference numerals 406, 408, 410, 412, 414 respectively. Here, the peak at about 26° C. such as generally represented by reference numeral 416 is a hexagonal graphitic peak that corresponds to C (002) plane of the carbon nanotubes. Moreover, the presence of additional peaks in the XRD patterns 408, 410, 412 and 414 for carbon nanotubes decorated with palladium nanoparticles, carbon nanotubes decorated with platinum nanoparticles, carbon nanotubes decorated with gold nanoparticles and carbon nanotubes decorated with silver nanoparticles represented formation of respective metal nanoparticles. The peaks were comparable with standard Joint Committee on Powder Diffraction Standards (JCPDS) patterns from International Centre for Diffraction Data (ICDD) i.e., Pd (JCPDS-89-4897), Pt (JCPDS-87-0646), Au (JCPDS-65-2870) and Ag (JCPDS-87-0720) indicating deposition of the nanoparticles on the carbon nanotubes.

The XRD patterns of plain carbon nanotubes, carbon nanotubes decorated with palladium cobalt alloy ($Pd_3Co$) nanoparticles, carbon nanotubes decorated with platinum cobalt alloy ($Pt_3Co$) nanoparticles, carbon nanotubes decorated with nickel oxide (NiO) nanoparticles and carbon nanotubes decorated with zinc oxide (ZnO) nanoparticles are represented by reference numerals 418, 420, 422, 424 and 426 respectively. Again, the XRD patterns of the carbon nanotubes decorated with metal oxides and metal alloys were comparable with corresponding JCPDS patterns. This indicated the decomposition of metal salt in presence of the focused solar radiation and simultaneous formation of metal oxide and alloys nano structures.

The XRD analyses of the carbon nanotubes decorated with metal nanoparticles, metal oxide nanoparticles, and metal alloy nanoparticles formed using the present technique indicated formation of stable crystal structures and complete reduction of metal salts to metal owing to the solar exposure. The focused solar radiation facilitated solar induced photo reduction of metal salts along with release of chlorine gas due to substantial rise in temperature.

Figure 5:
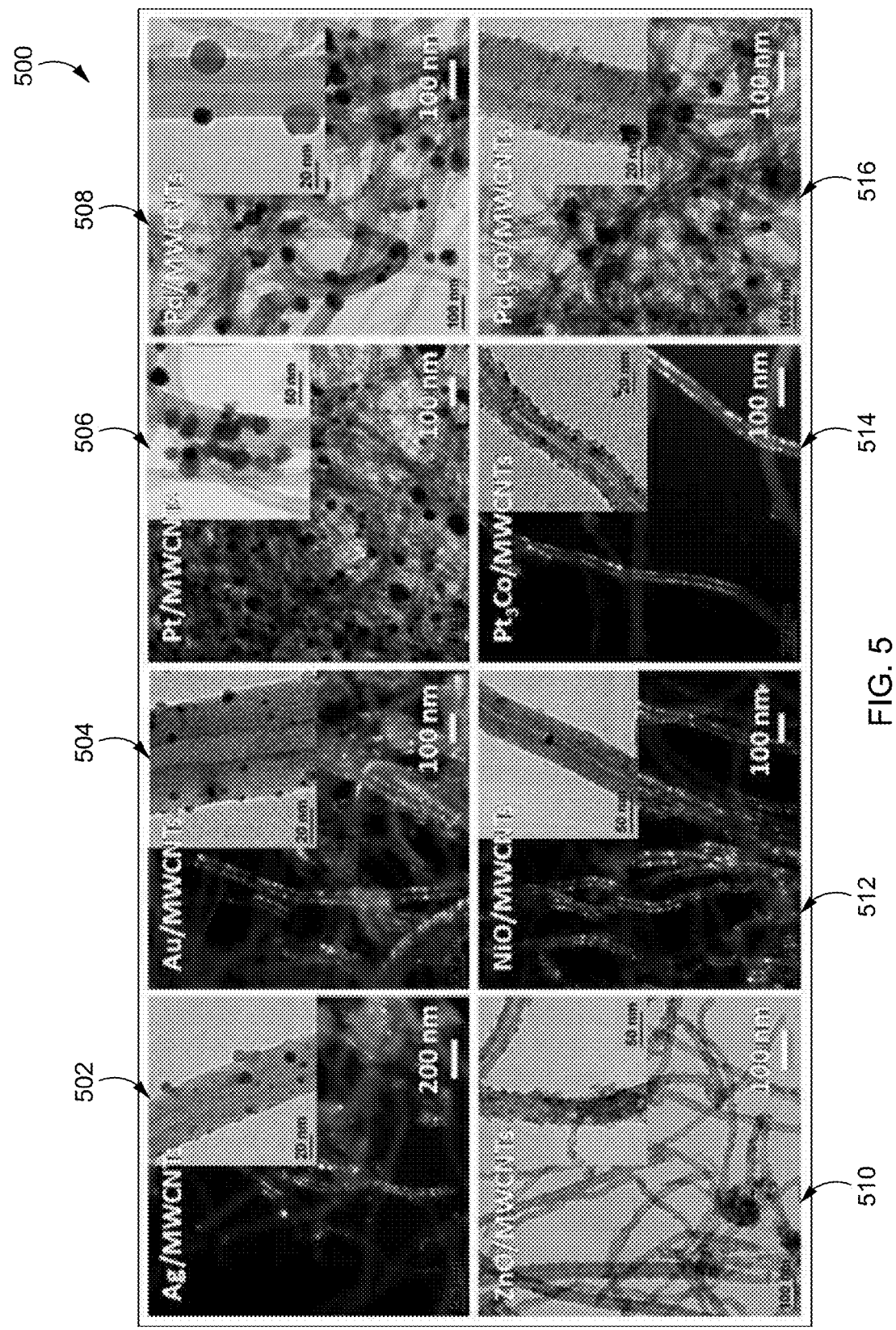
FIG. 5 illustrates example transmission electron microscopy (TEM) images for carbon nanotubes decorated with metal nanoparticles, metal oxide nanoparticles and metal alloy nanoparticles.

FIG. 5 illustrates example transmission electron microscopy (TEM) images 500 for carbon nanotubes decorated with metal nanoparticles, metal oxide nanoparticles and metal alloy nanoparticles. The TEM images for carbon nanotubes decorated with silver nanoparticles, carbon nanotubes decorated with gold nanoparticles, carbon nanotubes decorated with platinum nanoparticles, carbon nanotubes decorated with palladium nanoparticles, carbon nanotubes decorated with zinc oxide nanoparticles, carbon nanotubes decorated with nickel oxide nanoparticles, carbon nanotubes decorated with platinum cobalt alloy nanoparticles and carbon nanotubes decorated with palladium cobalt alloy nanoparticles are represented by 502, 504, 506, 508, 510, 512, 514 and 516 respectively.

As can be seen from the images 502, 504, 506, 508, 510, 512, 514 and 516, the respective metal, metal oxide and metal alloy nanoparticles deposited on the carbon nanotubes was clearly observed. The size of the deposited nanoparticles was estimated from high-resolution transmission electron microscopy (HRTEM) micrographs. The size of the deposited nanoparticles was measured to be about 2 nm to 10 nm for silver (Ag) and gold (Au) nanoparticles, about 10 nm to about 50 nm for platinum (Pt) and palladium (Pd) nanoparticles, about 5 nm to about 15 nm for zinc oxide (ZnO) nanoparticles, about 2 nm to about 5 nm for nickel oxide (NiO) nanoparticles, about 2 nm to about 10 nm for platinum cobalt alloy ($Pt_3Co$) nanoparticles, and about 2 nm to about 5 nm for palladium cobalt alloy $Pd_3Co$ nanoparticles.

Figure 6:
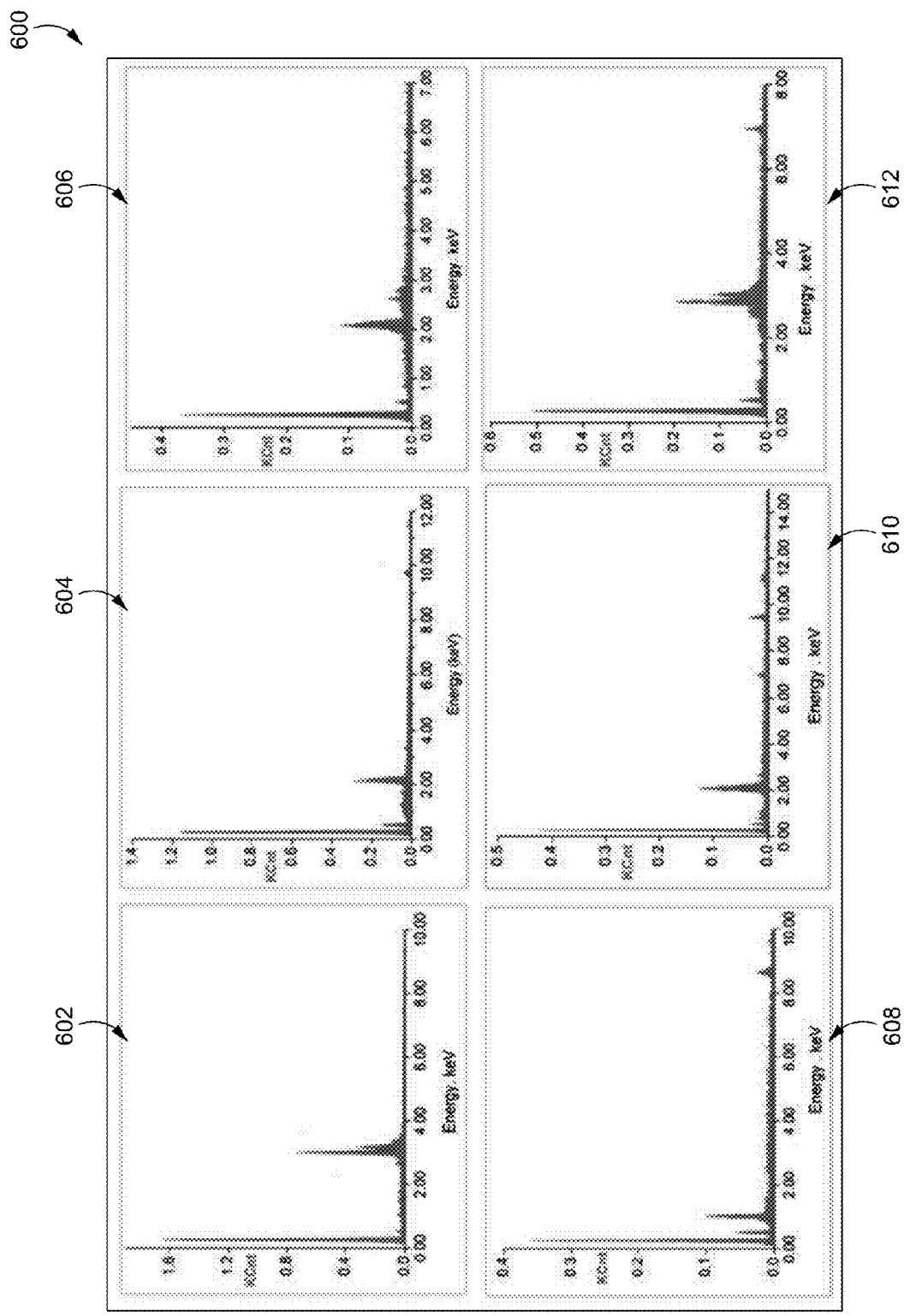
FIG. 6 illustrates example energy-dispersive X-ray spectroscopy (EDX) spectra of carbon nanotubes decorated with metal nanoparticles, metal oxide nanoparticles and metal alloy nanoparticles.

FIG. 6 illustrates example energy-dispersive X-ray spectroscopy (EDX) spectra 600 of carbon nanotubes decorated with metal nanoparticles, metal oxide nanoparticles and metal alloy nanoparticles. The EDX spectrum for carbon nanotubes decorated with silver nanoparticles, carbon nanotubes decorated with gold nanoparticles, carbon nanotubes decorated with platinum nanoparticles, carbon nanotubes decorated with zinc oxide nanoparticles, carbon nanotubes decorated with platinum cobalt alloy nanoparticles and carbon nanotubes decorated with palladium cobalt alloy nanoparticles are represented by 602, 604, 606, 608, 610, and 612 respectively. The EDX spectra 602, 604 and 606 confirm the presence of respective metal nanoparticles deposited on the carbon nanotubes. Similarly, the EDX spectra 608, 610, and 612 confirm the presence of corresponding metal oxide and metal alloy nanoparticles deposited on the carbon nanotubes. The EDX spectra 602, 604, 606, 608, 610, and 612 also indicated absence of chlorine or other unwanted metal salts.

Figure 7:
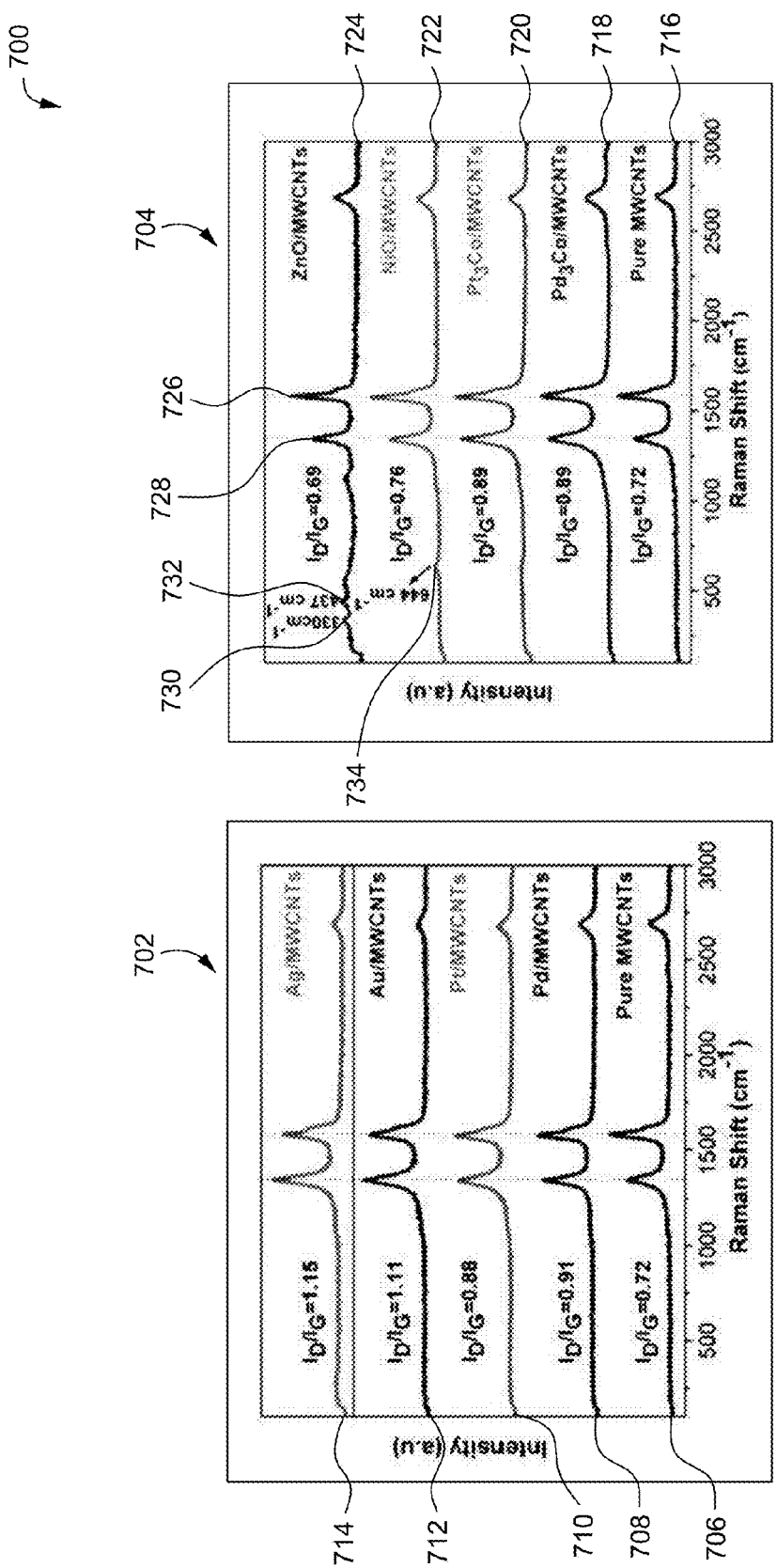
FIG. 7 illustrates example Raman spectra of plain carbon nanotubes, carbon nanotubes decorated with metal nanoparticles, metal oxide nanoparticles and metal alloy nanoparticles.

FIG. 7 illustrates example Raman spectra 700 of plain carbon nanotubes, carbon nanotubes decorated with metal nanoparticles, metal oxide nanoparticles and metal alloy nanoparticles. Here, Raman spectra for plain carbon nanotubes and for metal decorated carbon nanotubes are represented by reference numeral 702. Further, Raman spectra for plain carbon nanotubes and for metal alloy decorated carbon nanotubes are represented by reference numeral 704.

The Raman spectrum for plain carbon nanotubes, carbon nanotubes decorated with palladium nanoparticles, carbon nanotubes decorated with platinum nanoparticles, carbon nanotubes decorated with gold nanoparticles and carbon nanotubes decorated with silver nanoparticles are represented by reference numerals 706, 708, 710, 712, and 714 respectively. Further, Raman spectrum of plain carbon nanotubes, carbon nanotubes decorated with palladium cobalt alloy ($Pd_3Co$) nanoparticles, carbon nanotubes decorated with platinum cobalt alloy ($Pt_3Co$) nanoparticles, carbon nanotubes decorated with nickel oxide (NiO) nanoparticles and carbon nanotubes decorated with zinc oxide (ZnO) nanoparticles are represented by reference numerals 716, 718, 720, 722 and 724 respectively.

As can be seen, appearance of G-band in the Raman spectrum was observed at about 1590 $cm^{-1}$ (represented by reference numeral 726) which is a characteristic feature of graphitic layers corresponding to high frequency E2g first order mode. Moreover, additional band was observed at about 1300 $cm^{-1}$ (represented by reference numeral 728) that corresponds to a defect activated vibration D mode. The intensity ratio of D band and G band ($I_D/I_G$) is a measure of defects formed on the carbon nanotubes. The intensity ratio ($I_D/I_G$) was estimated and was shown on the Raman spectra 702 and 704. It should be noted that the increase in $I_D/I_G$ ratio for carbon nanotubes with deposition of different metal nanoparticles by solar reduction is indicative of attachment of nanoparticles over the surface of carbon nanotubes.

Further, in the spectrum 724 for carbon nanotubes decorated with zinc oxide (ZnO) nanoparticles additional peaks (generally represented by reference numerals 730 and 732) were observed at about 330 $cm^{-1}$ and about 437 $cm^{-1}$. The presence of peaks 730 and 732 may be due to zone boundary phonons and non-polar phonons. Similarly, for carbon nanotubes decorated with nickel oxide (NiO) nanoparticles, a strong peak at about 644 $cm^{-1}$ (generally represented by reference numeral 734) was observed, which may be due to the Ni—O stretching vibrational mode. The Raman spectra for alloy decorated carbon nanotubes showed the characteristic Raman bands for corresponding alloy nanostructures.

Example 3

Synthesis of Carbon Nanotubes-Graphene Composite Decorated with Zinc Oxide Nanoparticles A hybrid nanomaterial formed of carbon nanotubes-graphene composite decorated with zinc oxide nanoparticles was synthesized using the method shown in FIG. 1. Here, a mixture of a zinc precursor, graphite, and carbon nanotubes was exposed to focused solar radiation to reduce the zinc precursor and to concurrently reduce graphite oxide (GO) to solar graphene.

Graphite oxide (GO) was synthesized by Hummers method using flake graphite as the precursor. About 1 gm of flake graphite powder was refluxed in about 23 mL of concentrated sulphuric acid ($H_2SO_4$) and was continuously stirred in an ice bath. Subsequently, about 3 gm of potassium permanganate ($KMnO_4$) and about 0.5 gm of sodium nitrate ($NaNo_3$) were added to the suspension. The suspension was removed from the ice bath and was cooled to room temperature by adding about 47 ml of water to it. Moreover, about 3% of hydrogen peroxide ($H_2O_2$) was added to the suspension till it turned bright yellow color. The suspension was filtered and washed thoroughly by warm water and the final residue was dried in vacuum at a temperature of about 60° C.

Multi-walled carbon nanotubes (MWCNTs) were prepared by catalytic chemical vapor deposition (CVD) technique using acetylene as a carbon source and rare earth based mish metal ($MmNi_3$) as catalyst. The synthesized MWCNTs were air oxidized at a temperature of about 400° C. followed by acid treatment to remove amorphous carbon impurities and any remaining catalyst particles. The purified MWCNTs, GO, and zinc acetate salt were ground using a mortar to form a mixture.

Focused solar radiation was allowed to fall directly on the mixture for about 1 minute to 2 minutes using a convex lens of about 90 mm diameter. The high intensity of the focused solar radiation decomposed the zinc salt and simultaneously reduced GO to solar graphene resulting in a visible color change from brown to dark black with release of gaseous by products in the form of fumes during synthesis. As zinc is highly reactive, the formation of ZnO was attributed to decomposition of zinc acetate and its reaction with oxygen present in acetate based salt or open-air atmosphere. The temperature range during synthesis was maintained at about 250° C. to about 300° C. with a power range from about 1.77 W to 2.03 W.

Example 4

Characterization of Hybrid Material of Example 3

Figure 8:
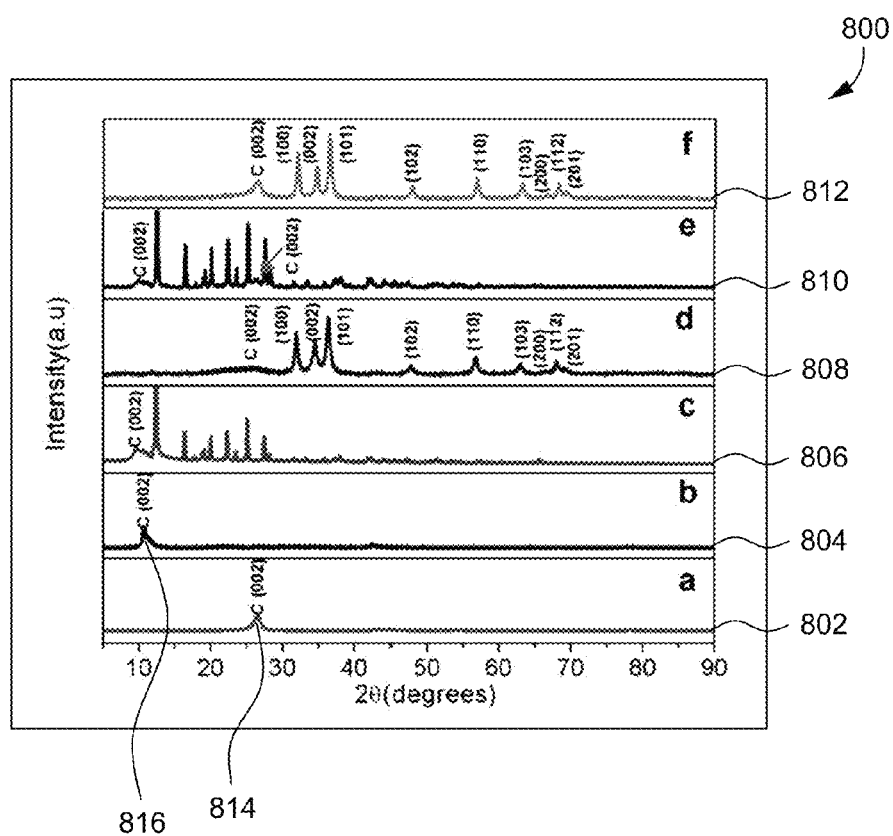
FIG. 8 illustrates example X-ray diffraction (XRD) pattern of pure carbon nanotubes, graphite oxide, mixture of graphite oxide and zinc precursor, and the synthesized hybrid material.

FIG. 8 illustrates example X-ray diffraction (XRD) pattern 800 of pure carbon nanotubes, graphite oxide, mixture of graphite oxide and zinc precursor, and the synthesized hybrid material. The synthesized hybrid material was formed of carbon nanotubes-graphene composite decorated with zinc oxide nanoparticles. The XRD patterns for pure MWCNTs, graphite oxide, mechanically mixed GO and zinc acetate, zinc oxide and solar graphene mixture, mechanically mixed GO and zinc acetate with MWCNTs and the hybrid material formed of carbon nanotubes-graphene decorated with zinc oxide nanoparticles are represented by reference numerals 802, 804, 806, 808, 810 and 812 respectively. The XRD patterns 800 were recorded using a PANalytical X'Pert Pro X-ray diffractometer with nickel-filtered Cu Kα radiation as the X-ray source in the 2θ range of 5° to 90° with 0.016° step size.

Here, the characteristic peak for pure MWCNTs was observed at 2θ value of about 26° (represented by reference numeral 814) corresponding to C (002) plane of hexagonal lattice. Moreover, the characteristic peak for GO was observed at 2θ value of about 11° (represented by reference numeral 816). Further, for the mechanical mixture of zinc acetate, MWCNT and GO additional peaks along with the peaks corresponding to MWCNT and GO were observed. Once the mixture was exposed to focused sun radiation, the peaks corresponding to MWCNT and GO had disappeared and about nine highly crystalline peaks in addition to a combined broaden and sharp peak corresponding to C (002) plane of solar graphene and MWCNTs were observed. The XRD pattern 800 was analyzed and it was observed that the pattern corresponded to hexagonal lattice pattern of ZnO (JCPDS-891397) indicating complete conversion of zinc salt to ZnO nanoparticles over two-dimensional graphene and one-dimensional MWCNT nanostructures.

Figure 9:
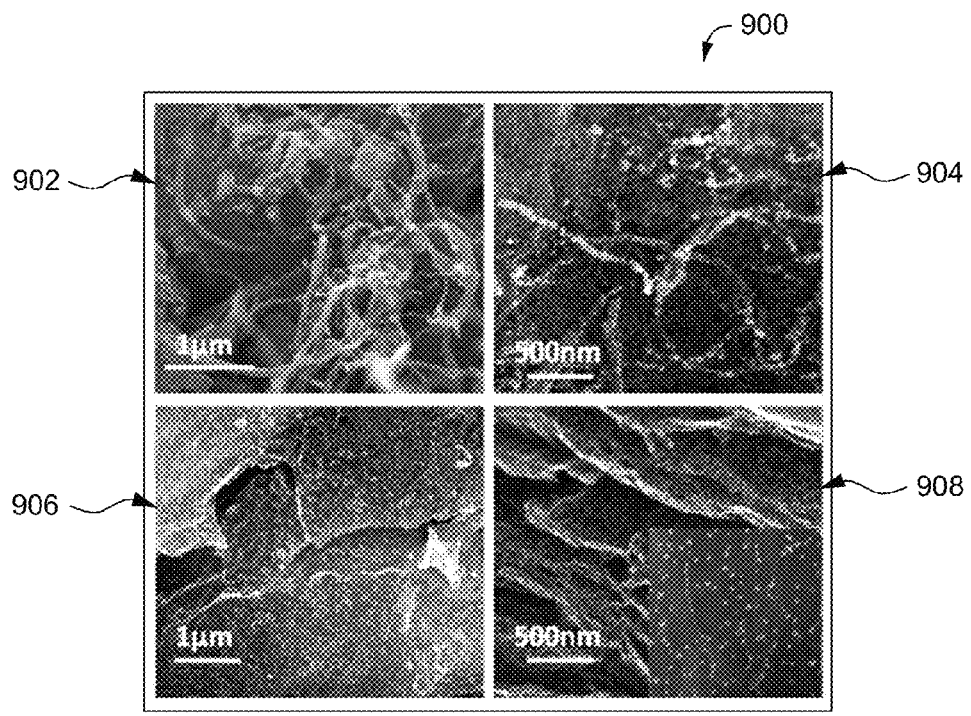
FIG. 9 illustrates example scanning electron microscope (SEM) images of carbon nanotubes-graphene composite and hybrid material formed of carbon nanotubes-graphene decorated with zinc oxide nanoparticles.

FIG. 9 illustrates example scanning electron microscope (SEM) images 900 of carbon nanotubes-graphene composite and hybrid material formed of carbon nanotubes-graphene composite decorated with zinc oxide nanoparticles. The SEM images of carbon nanotubes-graphene composite decorated with zinc oxide nanoparticles obtained at 1 micrometer (1 µm) and 500 nm resolutions are represented by reference numerals 902 and 904 respectively. The SEM images of carbon nanotubes-graphene composite obtained at 1 micrometer (1 µm) and 500 nm resolutions are represented by reference numerals 906 and 908 respectively. As can be seen, the zinc oxide nanoparticles are uniformly distributed over one-dimensional MWCNTs and two-dimensional solar graphene that enhanced the electrochemical activity of hybrid material.

Figure 10:
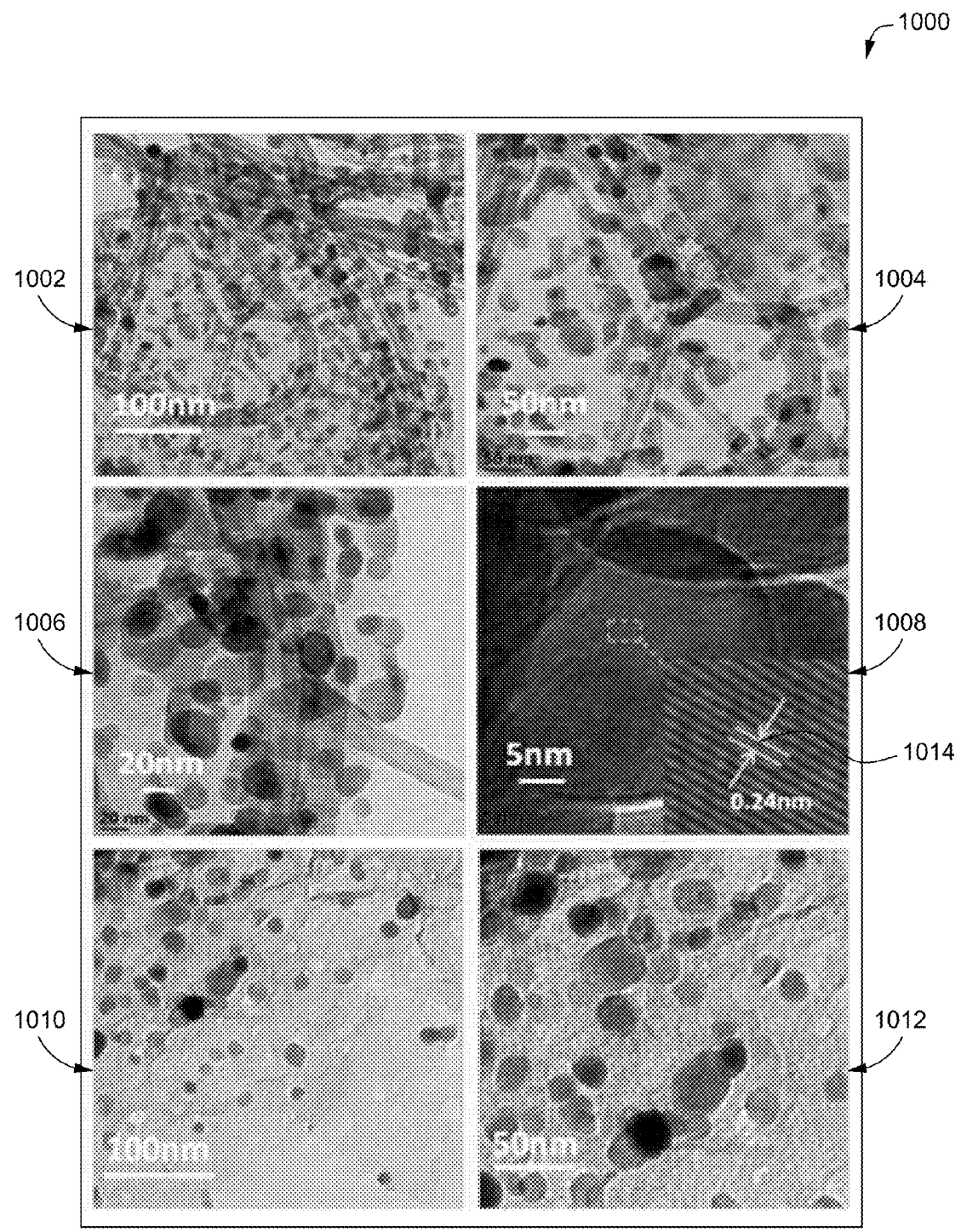
FIG. 10 illustrates example TEM images of carbon nanotubes-graphene composite and hybrid material formed of carbon nanotubes-graphene decorated with zinc oxide nanoparticles.

FIG. 10 illustrates example TEM images 1000 of carbon nanotubes-graphene composite and hybrid material formed of carbon nanotubes-graphene composite decorated with zinc oxide nanoparticles. The TEM images of carbon nanotubes-graphene composite decorated with zinc oxide nanoparticles obtained at different resolutions (100 nm, 50 nm, 20 nm and 5 nm) are represented by reference numerals 1002, 1004, 1006, and 1008 respectively. The TEM images of carbon nanotubes-graphene composite obtained at different resolutions (100 nm and 50 nm) are represented by reference numerals 1010 and 1012 respectively.

As can be seen from the TEM images 1000, the zinc oxide nanoparticles were uniformly distributed over the carbon nanotubes-graphene composite and had an average particle size of about 10 nm to about 60 nm. The deposited zinc oxide nanoparticles were observed to be spherical in shape. Further, as can be seen from image 1014, a clear lattice spacing of about 0.24 nm indicated high crystallinity of zinc oxide nanoparticles. The presence of MWCNTs in the hybrid structures acted as a spacer between graphene layers thereby increasing the overall surface area of graphene. This enhanced the electrocatalytic activity of the hybrid material making it suitable for bio-sensing, and energy related applications.

Figure 11:
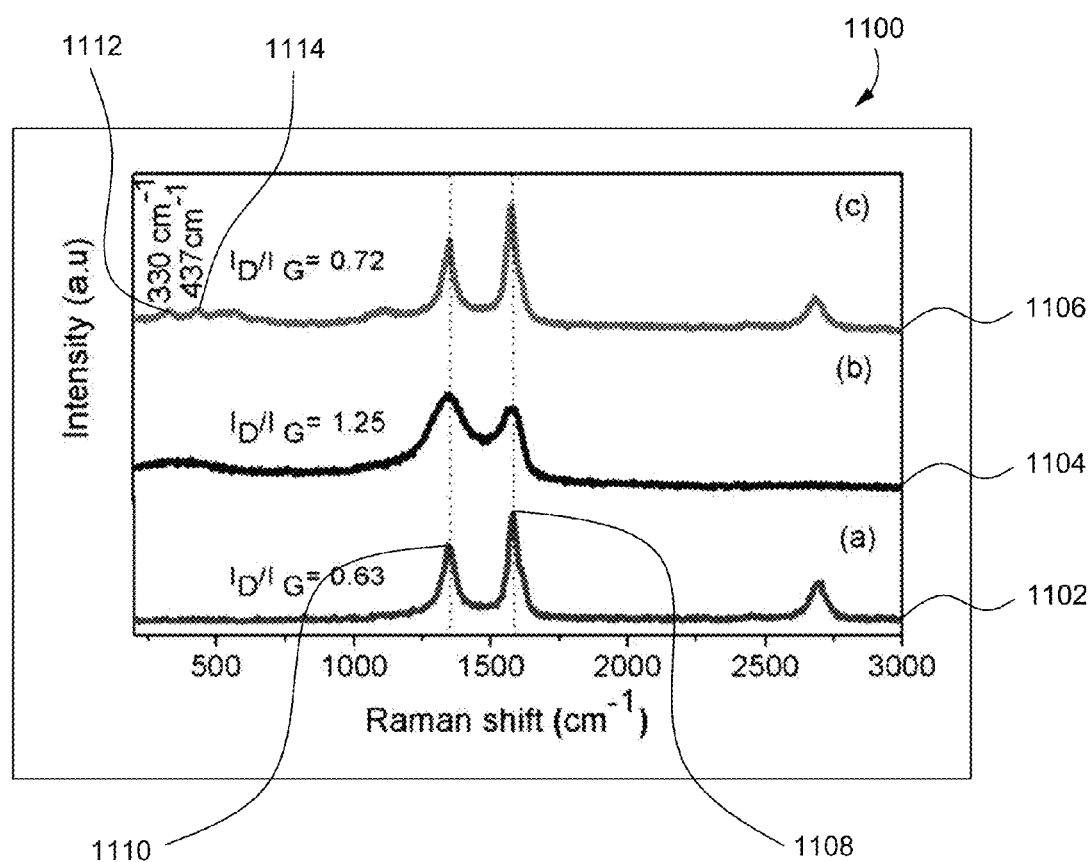
FIG. 11 illustrates example Raman spectra of plain carbon nanotubes, graphite oxide (GO) and the synthesized hybrid material.

FIG. 11 illustrates example Raman spectra 1100 of plain carbon nanotubes, graphite oxide (GO) and the synthesized hybrid material. The spectra for plain carbon nanotubes, GO and the hybrid material formed of carbon nanotubes-graphene composite decorated with zinc oxide nanoparticles are represented by reference numeral 1102, 1104 and 1106 respectively. A peak at about 1582 cm$^{-1}$ (represented by reference numeral 1108) was observed for plain carbon nanotubes that corresponded to the $E_{2G}$ vibrational mode of graphitic carbon. The defect induced D band was observed at about 1345 cm$^{-1}$ (represented by reference numeral 1110) indicative of the presence of disorder carbon atoms and surface modifications.

The peak intensity of the D band is a measure to scale the defects on the modified structures. For GO, the D band peak was observed to be dominant over G band ($I_D/I_G=1.25$) that may be due to the presence of oxygen containing functional groups in GO. Moreover for the hybrid material, the intensity of D band again was observed to be significant ($I_D/I_G=0.72$) that indicated the decoration of zinc oxide nanoparticles over solar graphene and carbon nanotubes. Again, two additional peaks (represented by reference numerals 1112 and 1114) were observed at about 330 cm$^{-1}$ and at about 437 cm$^{-1}$ corresponding to $E_2$ resonance mode and Al (LO) mode of ZnO nanoparticles.

Figure 12:
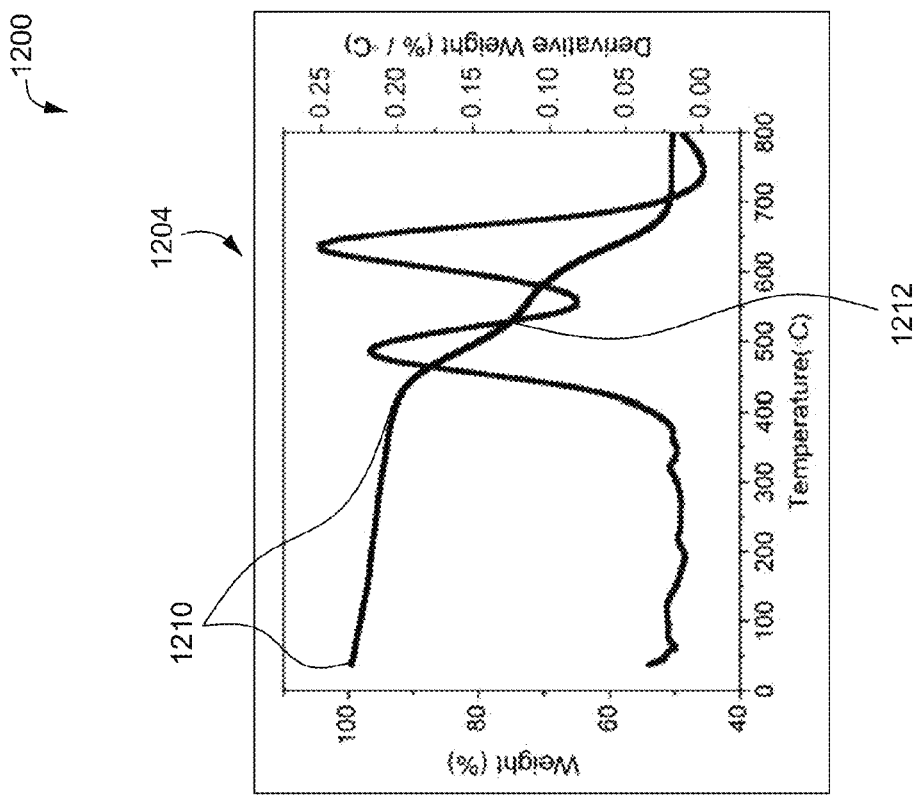
FIG. 12 illustrates example thermo gravimetric analysis (TGA) spectra for mixture of zinc acetate, multi-walled carbon nanotubes (MWCNTs) and graphite oxide (GO) and the hybrid material synthesized using focused solar radiation.
Figure 12:
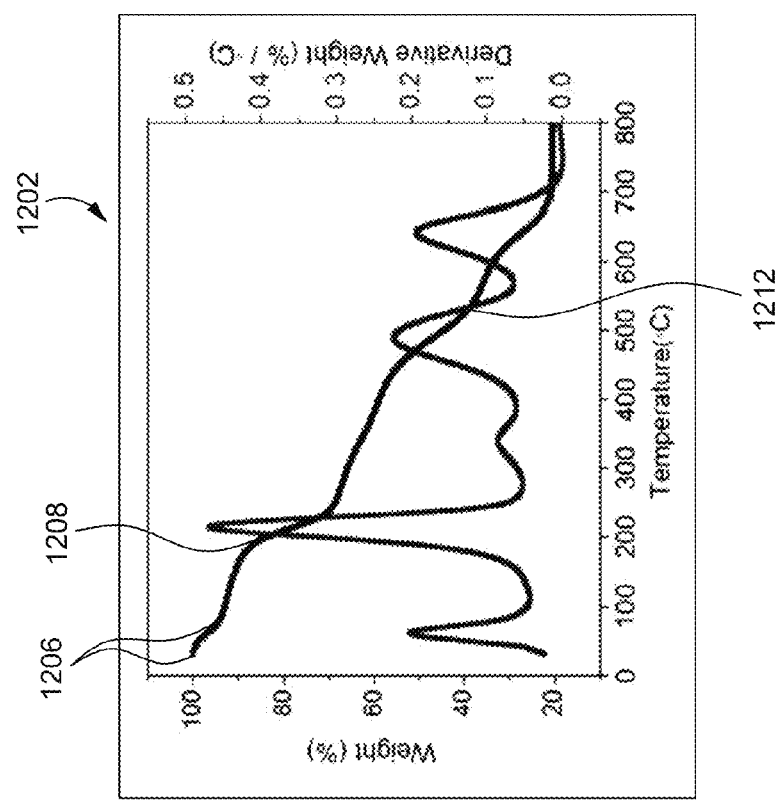

FIG. 12 illustrates example thermo gravimetric analysis (TGA) spectra 1200 for mixture of zinc acetate, multi-walled carbon nanotubes (MWCNTs) and graphite oxide (GO) and the synthesized hybrid material formed using focused solar radiation. The TGA spectrum for a mechanical mixture of zinc acetate, MWCNTs and GO is represented by reference numeral 1202. Further, the TGA spectrum for the hybrid material formed of carbon nanotubes-graphene composite decorated with zinc oxide nanoparticles using the focused solar radiation is represented by reference numeral 1204. Here, a weight loss below a temperature of about 100° C. (represented by reference numeral 1206) was observed for the mechanical mixture that may be due to decomposition of water present in hydrated zinc salt. Moreover, a substantial weight loss was observed at a temperature of about 220° C. (represented by reference numeral 1208) that may be due to decomposition of zinc acetate and oxygen containing functional groups of GO.

However, no sign of substantial weight loss was observed for the hybrid material below a temperature of 450° C. (represented by reference numeral 1210) indicative of complete reduction of zinc salt in the synthesized hybrid material. It should be noted that a two-step weight loss was observed at a temperature of about 480° C. for both the mechanical mixture and the synthesized hybrid material (represented by reference numeral 1212) that may be due to decomposition of graphene followed by MWCNTs. The loading of zinc oxide nanoparticles in the hybrid nanomaterial was measured from TGA spectra to be about 50%.

Example 5

Figure 13:
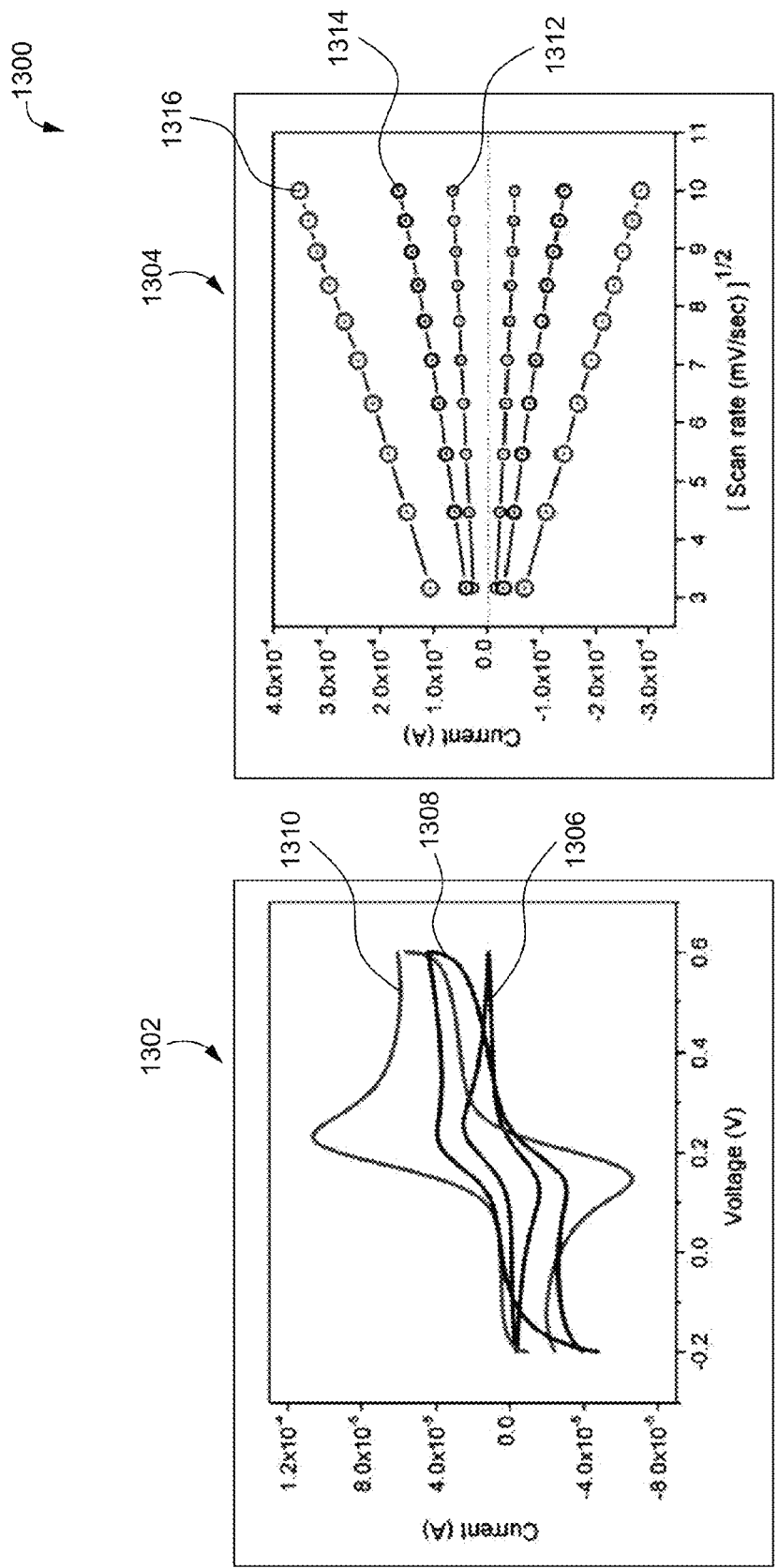
FIG. 13 illustrates example results for electrocatalytic activity for bare Glassy Carbon Electrode (GCE), zinc oxide-solar graphene GCE and the hybrid material GCE.

Characterization of Electrocatalytic Activity for Bare Glassy Carbon Electrode (GCE), Zinc Oxide-Solar Graphene GCE and the Hybrid Material GCE FIG. 13 illustrates example results 1300 for electrocatalytic activity for bare GCE, zinc oxide-solar graphene GCE and the hybrid material GCE. Here, cyclic voltammetry was used to study the electrocatalytic activity. The cyclic voltamogram and a graphical representation of measured redox peak current are represented by reference numerals 1302 and 1304 respectively. The voltamogram of bare GCE, zinc oxide-solar graphene GCE and the hybrid material GCE obtained for 5 mM potassium ferrocyanide ($K_4$ [Fe(CN)$_6$]) at about 10 mV/sec scan rate in about 1 mM KCl as supporting electrolyte are represented by reference numerals 1306, 1308, 1310 respectively.

$$Ip=2.69\times10^5 AD^{1/2}n^{3/2}\gamma^{1/2}C \quad (1)$$

where, γ is a scan rate in mV/sec,
D is diffusion coefficient(=6.7×10$^{-6}$ cm$^2$/sec),
n is number of electrons participating in reaction,
A is active surface area of electrode.

The active surface area (A) value estimated from the above equation for the hybrid material GCE was about 30.88 mm$^2$ and that for zinc oxide-solar graphene GCE was about 11.60 mm$^2$ that is substantially large as compared to that for bare GCE (about 7.067 mm$^2$). This enhancement in accessible surface area may be due to presence of MWCNTs that may physically separate the graphene sheets from aggregation.

A profile of redox peak current versus square root of scan rate obtained for bare GCE, zinc oxide-solar graphene GCE and the hybrid material GCE are represented by reference numerals 1312, 1314, and 1316 respectively. As can be seen, the redox peak current increased linearly indicating the charge transport to be diffusion controlled. The slope of the profile for the hybrid material was observed to be relatively high as compared to that of the zinc oxide-solar graphene GCE and bare GCE. This indicated enhanced electrocatalytic activity of the hybrid material that can be used as a transducer for fabrication of organophosphorus sensor.

Figure 14:
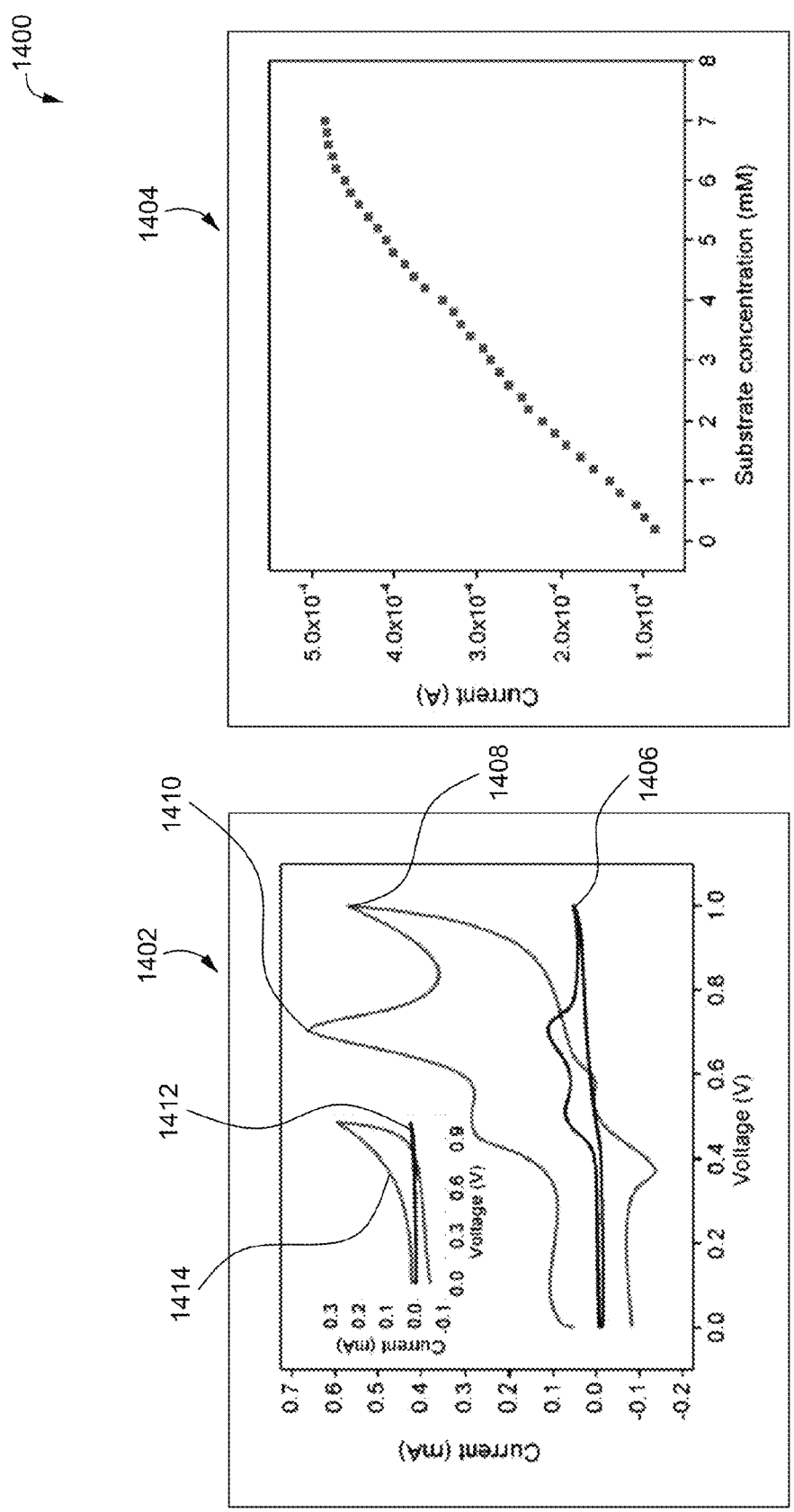
FIG. 14 illustrates an example cyclic voltamogram for 3 mM thiocholine with zinc oxide-solar graphene GCE and the hybrid material GCE.

FIG. 14 illustrates an example cyclic voltamogram 1400 for 3 mM thiocholine with zinc oxide-solar graphene GCE and the hybrid material GCE. The cyclic voltamograms for the two materials used for the GCE are represented by profiles 1402. Here, the cyclic voltamogram with zinc oxide-solar graphene GCE and with the hybrid material GCE in presence of 3 mM thiocholine solution prepared by enzymatic reaction of AChE and Acetylcholine iodide (AChI) are represented by reference numerals 1404 and 1406 respectively.

As can be seen, a sharp oxidation peak was observed at about 0.67 V (represented by reference numeral 1410) for the hybrid material GCE as compared to that of zinc oxide-solar graphene GCE, which is indicative of its catalytic activity towards thiocholine oxidation. Additionally, the oxidation current for the hybrid material GCE is about 4 folds greater than that of zinc oxide-solar graphene GCE electrode along with a pair of redox peak at lower potential which may be due to presence of iodide redox couple.

Moreover, the inset shows the cyclic voltamogram with zinc oxide-solar graphene GCE (represented by reference numeral 1412) and with the hybrid material GCE (represented by reference numeral 1414) in presence of phosphate buffered saline (PBS) with a pH 7.4 used as supporting electrolyte.

Further, a substrate response with the hybrid material GCE towards different concentration of the AChI solution is represented by profile 1406. As can be seen, the response of the measured current varied linearly for concentration of about 0.2 mM to about 6.4 mM. The Michaelis-Menten constant (Km) estimated from following equation was about 0.8 mM:

$$I = I_{max} - K_m(I/[S])  \quad (2)$$

where, $I_{max}$ is the maximum current obtained,
I is the steady state current,
S is the substrate concentration,
$K_m$ is the Michaelis-Menten constant.

The relatively low value of $K_m$ was indicative of a measure of efficient conversion of substrate to product by the enzyme that may be due to better enzyme adhesion on the hybrid nanomaterial retaining its activity. Also as ZnO nanoparticles have high isoelectric point (IEP=9.5), they could facilitate efficiently binding of the AChE enzyme (IEP=4.5) in phosphate buffer environment (with pH of about 7.4) retaining its bioactivity.

Example 6

Effect of Different Concentration of Paraoxon on Inhibition Current of a Sensor

Figure 15:
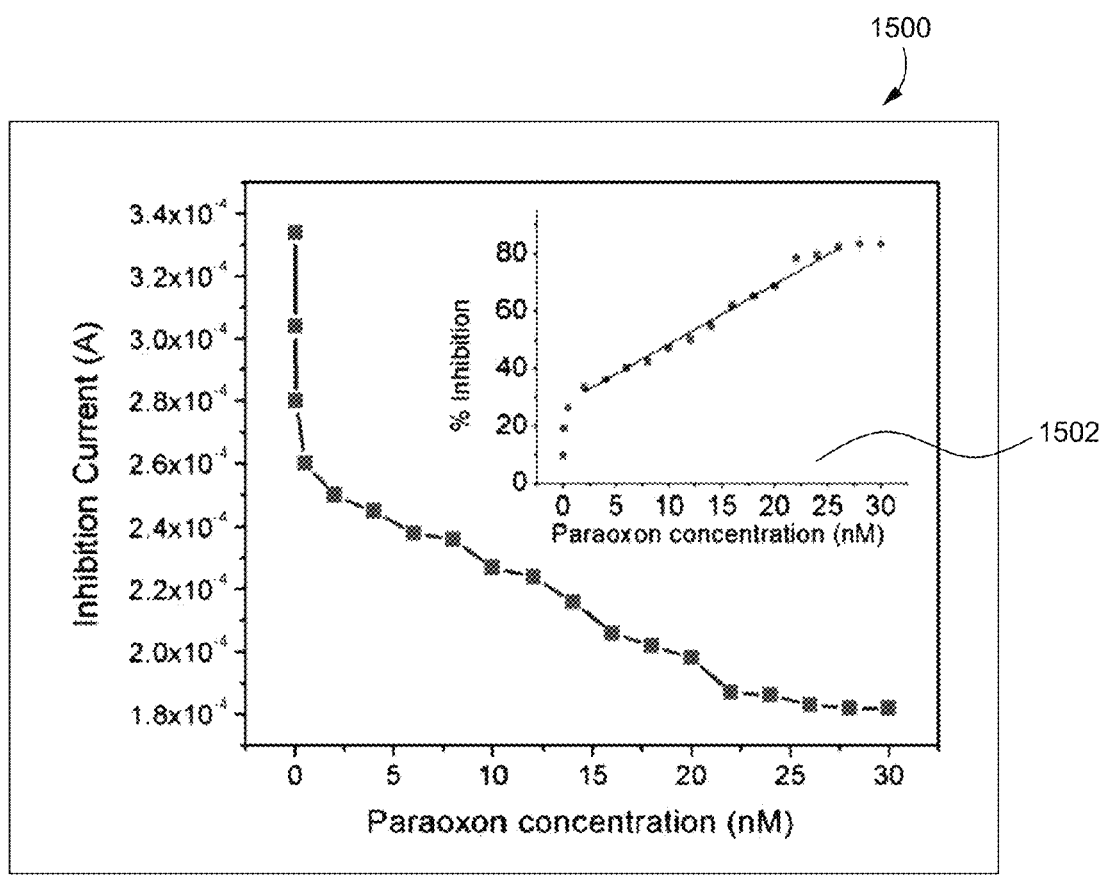
FIG. 15 illustrates an example graphical representation of variation of inhibition current with different concentration levels of paraoxon.

FIG. 15 illustrates an example graphical representation 1500 of variation of inhibition current with different concentration levels of paraoxon. As can be seen, the inhibition current decreases sharply with addition of paraoxon. This indicated the decrease in catalytic activity of the enzyme AChE after exposure to paraoxon. The inset of FIG. 15 shows a graphical representation 1502 of percentage of inhibition current with different concentration levels of paraoxon. The percentage of inhibition current was estimated using the following equation:

$$\% \text{ Inhibition} = [(I_{max} - I_{in})/I_{max}] \times 100, \quad (3)$$

where, $I_{max}$ is the maximum current measured in presence of about 3 mM AChI solution,
$I_{in}$ is the current measured after incubation with paraoxon for about 5 minutes.

A linear response for a concentration of about 1 nM to about 26 nM was obtained with a detection limit of about 1 pM (S/N=3). The lower detection limit may be attributed to the functionality of the hybrid matrix to hold the enzyme.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible sub ranges and combinations of sub ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

As will also be understood by one skilled in the art all language such as "up to," "at least," "greater than," "less than," and the like include the number recited and refer to ranges which can be subsequently broken down into sub ranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of forming carbon nanotubes decorated with nanoparticles, the method comprising:
   mixing a metal precursor with a plurality of carbon nanotubes to form a metal precursor-carbon nanotubes mixture; and
   exposing the metal precursor-carbon nanotubes mixture to electromagnetic radiation to deposit the metal precursor as the nanoparticles on a major surface of the carbon nanotubes, wherein the nanoparticles comprise a metal alloy nanoparticle, and one or more of a metal nanoparticle and a metal oxide nanoparticle.

2. The method of claim 1, wherein mixing the metal precursor with the plurality of carbon nanotubes comprises mixing the carbon nanotubes with the metal precursor selected from the group consisting of silver acetate ($CH_3COOAg$), silver chloride (AgCl), silver nitrate ($AgNO_3$), chloroauric acid ($HAuCl_4$), hexachloroplatinic acid ($H_2PtCl_6 \cdot (H_2O)_6$), palladium chloride ($PdCl_2$), nickel acetate tetrahydrate ($Ni(CH_3COO)_2 \cdot 4H_2O$), nickel chloride ($NiCl_2$), zinc acetate dihydrate ($Zn(O_2CCH_3)_2 \cdot 2H_2O$), zinc nitrate ($Zn(NO_3)_2$), cobalt nitrate hexahydrate ($Co(NO_3)_2 \cdot 6H_2O$), cobalt chloride ($CoCl_2$), and combinations thereof.

3. The method of claim 1, wherein exposing comprises exposing the metal precursor-carbon nanotubes mixture to electromagnetic radiation to deposit the metal precursor as nanoparticles, wherein the nanoparticles are selected from the group consisting of platinum (Pt), palladium (Pd), silver (Ag), gold (Au), nickel (Ni), titanium (Ti), tin (Sn), ruthenium (Ru), zinc (Zn), copper (Cu), zinc oxide (ZnO), nickel oxide (NiO), copper oxide (CuO), iron oxide ($Fe_3O_4$), cobalt oxide ($CoO_3$), titanium oxide ($TiO_2$), cerium oxide ($CeO_2$), manganese dioxide ($MnO_2$), platinum cobalt alloy ($Pt_3Co$), platinum nickel alloy ($Pt_3Ni$), palladium cobalt alloy ($Pd_3Co$), palladium iron alloy ($Pd_3Fe$), platinum iron alloy ($Pt_3Fe$), and combinations thereof.

4. The method of claim 1, wherein exposing the metal precursor-carbon nanotubes mixture to electromagnetic radiation comprises exposing the metal precursor-carbon nanotubes mixture to solar radiation.

5. A nanoparticle decorated carbon nanotubes formed by exposing a mixture of a metal precursor and a plurality of carbon nanotubes to electromagnetic radiation to deposit the metal precursor as nanoparticles on a major surface of the plurality of carbon nanotubes, wherein the nanoparticles comprise a metal alloy nanoparticle, and one or more of a metal nanoparticle and a metal oxide nanoparticle.

6. The nanoparticle decorated carbon nanotubes of claim 5, wherein the metal precursor comprises silver acetate ($CH_3COOAg$), silver chloride (AgCl), silver nitrate ($AgNO_3$), chloroauric acid ($HAuCl_4$), hexachloroplatinic acid ($H_2PtCl_6 \cdot (H_2O)_6$), palladium chloride ($PdCl_2$), nickel acetate tetrahydrate ($Ni(CH_3COO)_2 \cdot 4H_2O$), nickel chloride ($NiCl_2$), zinc acetate dihydrate ($Zn(O_2CCH_3)_2 \cdot 2H_2O$), zinc nitrate ($Zn(NO_3)_2$), cobalt nitrate hexahydrate ($Co(NO_3)_2 \cdot 6H_2O$), cobalt chloride ($CoCl_2$), or combinations thereof.

7. The nanoparticle decorated carbon nanotubes of claim 5, wherein the nanoparticles comprise platinum (Pt), palladium (Pd), silver (Ag), gold (Au), nickel (Ni), titanium (Ti), tin (Sn), ruthenium (Ru), zinc (Zn), copper (Cu), zinc oxide (ZnO), nickel oxide (NiO), copper oxide (CuO), iron oxide ($Fe_3O_4$), cobalt oxide ($CoO_3$), titanium oxide ($TiO_2$), cerium oxide ($CeO_2$), manganese dioxide ($MnO_2$), platinum cobalt alloy ($Pt_3Co$), platinum nickel alloy ($Pt_3Ni$), palladium cobalt alloy ($Pd_3Co$), palladium iron alloy ($Pd_3Fe$), platinum iron alloy ($Pt_3Fe$), or combinations thereof.

8. The nanoparticle decorated carbon nanotubes of claim 5, wherein the nanotube comprises a plurality of carbon nanotubes comprising single-walled carbon nanotubes, multi-walled carbon nanotubes, or combinations thereof.

9. The nanoparticle decorated carbon nanotubes of claim 5, wherein a size of the nanoparticles is about 2 nanometers (nm) to about 50 nm.

10. A method of forming a nanoparticle decorated carbon nanotubes-graphene composite, the method comprising:
    mixing a metal precursor with graphite oxide and a plurality of carbon nanotubes to form a mixture; and
    exposing the mixture to solar radiation to reduce graphite oxide to graphene and to form a carbon nanotubes-graphene composite and to concurrently reduce the metal precursor to nanoparticles, and to deposit the nanoparticles on a major surface of the carbon nanotubes-graphene composite, wherein the nanoparticles comprise a metal alloy nanoparticle, and one or more of a metal nanoparticle and a metal oxide nanoparticle.

11. The method of claim 10, wherein the mixing comprises mixing the graphite oxide and the plurality of carbon nanotubes with the metal precursor selected from the group consisting of zinc acetate ($Zn(O_2CCH_3)_2$), zinc chloride ($ZnCl_2$), and combinations thereof.

12. The method of claim 10, wherein the mixing comprises mixing the graphite oxide and the metal precursor with a plurality of multi-walled carbon nanotubes.

13. A sensor comprising:
    a composite material comprising carbon nanotubes and graphene; and nanoparticles deposited on a major surface of the carbon nanotubes of the composite material, wherein the nanoparticles comprise a metal alloy nanoparticle, and one or more of a metal nanoparticle and a metal oxide nanoparticle.

14. The sensor of claim 13, wherein the nanoparticles are deposited by exposing a mixture of a metal precursor, graphite oxide and a plurality of carbon nanotubes to electromagnetic radiation.

15. The sensor of claim 14, wherein the electromagnetic radiation comprises solar radiation.

16. The sensor of claim 13, wherein the sensor is configured to detect an organophosphorus compound in a medium, and wherein the organophosphorus compound is present in a concentration range of about 1 nanomolar (nM) to about 1 picomolar (pM).

17. The sensor of claim 16, wherein the organophosphorus compound comprises paraoxon, parathion, carbaryl, malathion, or combinations thereof.

18. The sensor of claim 13, wherein a size of the nanoparticle is about 10 nm to about 60 nm.

19. The sensor of claim 13, wherein an active surface area of the sensor is about 30 mm$^2$.

20. A method for detecting an organophosphorus compound in a medium, the method comprising:
   contacting a sensor with the medium, wherein the sensor comprises a composite material comprising carbon nanotubes and graphene, and wherein a plurality of nanoparticles are deposited on a major surface of the carbon nanotubes, wherein the nanoparticles comprise a metal alloy nanoparticle, and one or more of a metal nanoparticle and a metal oxide nanoparticle; and
   sensing an inhibition current by the sensor to detect the presence and a concentration of the organophosphorus compound in the medium.

21. The method of claim 20, wherein depositing the plurality of nanoparticles is by exposing a mixture of a zinc metal precursor, graphite oxide and a plurality of carbon nanotubes to electromagnetic radiation.

22. The method of claim 20, wherein the sensing comprises sensing the inhibition current by the sensor to detect the presence and the concentration of paraoxon, parathion, carbaryl, malathion or combinations thereof, in a concentration range of about 1 nM to about 1 pM.

23. The method of claim 20, wherein the inhibition current sensed by the sensor is about 33% to about 82%.

* * * * *